(12) United States Patent
Jones et al.

(10) Patent No.: US 12,290,272 B2
(45) Date of Patent: May 6, 2025

(54) TIBIAL CUT GUIDE

(71) Applicant: Zimmer, Inc., Warsaw, IN (US)

(72) Inventors: Nolan C. Jones, Warsaw, IN (US); Lindsey R. Rolston, New Castle, IN (US); Jeffery A. VanDiepenbos, New Paris, IN (US); Brian D. Earl, South Bend, IN (US); Anthony Romano, Columbia City, IN (US); Andrew Freiberg, Weston, MA (US)

(73) Assignee: Zimmer, Inc., Warsaw, IN (US)

( * ) Notice: Subject to any disclaimer, the term of this patent is extended or adjusted under 35 U.S.C. 154(b) by 307 days.

(21) Appl. No.: 17/853,492

(22) Filed: Jun. 29, 2022

(65) Prior Publication Data

US 2022/0330956 A1  Oct. 20, 2022

Related U.S. Application Data

(63) Continuation of application No. 16/687,171, filed on Nov. 18, 2019, now Pat. No. 11,406,400, which is a
(Continued)

(51) Int. Cl.
*A61B 17/17* (2006.01)
*A61B 17/15* (2006.01)
*A61F 2/46* (2006.01)

(52) U.S. Cl.
CPC ........ *A61B 17/1764* (2013.01); *A61B 17/157* (2013.01); *A61F 2/461* (2013.01)

(58) Field of Classification Search
CPC .......................... A61B 17/157; A61B 17/1764
See application file for complete search history.

(56) References Cited

U.S. PATENT DOCUMENTS

| | | |
|---|---|---|
| 5,628,750 A | 5/1997 | Whitlock et al. |
| 7,641,663 B2 | 1/2010 | Hodorek |
| | (Continued) | |

FOREIGN PATENT DOCUMENTS

| | | |
|---|---|---|
| CN | 101466317 A | 6/2009 |
| CN | 107920825 A | 4/2018 |
| | (Continued) | |

OTHER PUBLICATIONS

"U.S. Appl. No. 15/184,016, Advisory Action mailed Nov. 5, 2018", 3 pgs.
(Continued)

*Primary Examiner* — Olivia C Chang
(74) *Attorney, Agent, or Firm* — Schwegman Lundberg & Woessner, P.A.

(57) ABSTRACT

Methods and apparatuses including apparatuses that can be used in a unicompartmental knee replacement procedure, a bicompartmental knee replacement procedure comprised of two unicompartmental knee replacements, a knee replacement procedure that utilizes a single femoral component and two unicompartmental tibial components, and other types of knee replacement procedures are disclosed. According to one example, an apparatus for guiding a tibial bone cut during knee replacement surgery is disclosed. The apparatus can comprise a mounting portion and a cutting portion. The mounting portion can be configured to couple with an alignment mechanism. The cutting portion can be connected to the mounting portion and can define a capture for a proximal cut. The cutting portion can have an aperture disposed adjacent a first end of the capture.

13 Claims, 14 Drawing Sheets

Related U.S. Application Data continuation of application No. 15/184,016, filed on Jun. 16, 2016, now Pat. No. 10,517,614.

(60) Provisional application No. 62/182,073, filed on Jun. 19, 2015.

(56) References Cited

U.S. PATENT DOCUMENTS

| | | |
|---|---|---|
| 8,317,797 B2 | 11/2012 | Rasmussen |
| 8,758,354 B2 | 6/2014 | Habegger et al. |
| 10,245,046 B2 | 4/2019 | Jaumard et al. |
| 10,285,714 B2 | 5/2019 | Branscome et al. |
| 10,357,256 B2 | 7/2019 | Branscome et al. |
| 10,517,614 B2 | 12/2019 | Jones et al. |
| 11,272,942 B2 | 3/2022 | Branscome et al. |
| 11,406,400 B2 | 8/2022 | Jones et al. |
| 2006/0184173 A1 | 8/2006 | Collazo |
| 2007/0233138 A1 | 10/2007 | Figueroa et al. |
| 2012/0179266 A1 | 7/2012 | Collazo |
| 2012/0316563 A1 | 12/2012 | Metzger et al. |
| 2013/0204260 A1 | 8/2013 | Dietzel et al. |
| 2014/0066934 A1 | 3/2014 | Deirmengian et al. |
| 2014/0257310 A1* | 9/2014 | Trachsler ............ A61B 17/157 606/88 |
| 2015/0196308 A1 | 7/2015 | Wilkinson et al. |
| 2015/0342742 A1 | 12/2015 | Ferro et al. |
| 2016/0367271 A1 | 12/2016 | Jones et al. |
| 2017/0135708 A1 | 5/2017 | Jaumard et al. |
| 2018/0070960 A1 | 3/2018 | Branscome et al. |
| 2018/0070961 A1 | 3/2018 | Branscome et al. |
| 2019/0290293 A1 | 9/2019 | Branscome et al. |
| 2020/0085451 A1 | 3/2020 | Jones et al. |

FOREIGN PATENT DOCUMENTS

| | | |
|---|---|---|
| EP | 3310271 B1 | 7/2024 |
| GB | 2480846 A | 12/2011 |
| WO | WO-2008091358 A1 | 7/2008 |
| WO | WO-2012158604 A1 | 11/2012 |
| WO | WO-2013063375 A1 | 5/2013 |
| WO | WO-2014026082 A1 | 2/2014 |
| WO | WO-2016205454 A1 | 12/2016 |
| WO | WO-2018052843 A1 | 3/2018 |

OTHER PUBLICATIONS

"U.S. Appl. No. 15/184,016, Examiner Interview Summary mailed May 29, 2019", 3 pgs.
"U.S. Appl. No. 15/184,016, Final Office Action mailed Aug. 29, 2018", 15 pgs.
"U.S. Appl. No. 15/184,016, Non Final Office Action mailed Feb. 26, 2019", 12 pgs.
"U.S. Appl. No. 15/184,016, Non Final Office Action mailed May 2, 2018", 16 pgs.
"U.S. Appl. No. 15/184,016, Notice of Allowance mailed Aug. 20, 2019", 6 pgs.
"U.S. Appl. No. 15/184,016, Response Filed May 23, 2019 to Non-Final Office Action Mailed Feb. 26, 2019", 14 pgs.
"U.S. Appl. No. 15/184,016, Response filed Aug. 8, 2018 to Non Final Office Action mailed May 2, 2018", 15 pgs.
"U.S. Appl. No. 15/184,016, Response Filed Oct. 29, 2018 to Final Office Action Mailed Aug. 29, 2018", 15 pgs.
"U.S. Appl. No. 15/266,311, Corrected Notice of Allowability mailed Jan. 30, 2019", 3 pgs.
"U.S. Appl. No. 15/266,311, Corrected Notice of Allowability mailed Apr. 9, 2019", 3 pgs.
"U.S. Appl. No. 15/266,311, Non Final Office Action mailed Aug. 30, 2018", 10 pgs.
"U.S. Appl. No. 15/266,311, Notice of Allowance mailed Jan. 3, 2019", 6 pgs.
"U.S. Appl. No. 15/266,311, Response filed Nov. 26, 2018 to Non Final Office Action mailed Aug. 30, 2018", 10 pgs.
"U.S. Appl. No. 15/341,306, Non Final Office Action mailed Aug. 28, 2018", 8 pgs.
"U.S. Appl. No. 15/341,306, Notice of Allowance mailed Nov. 29, 2018", 6 pgs.
"U.S. Appl. No. 15/341,306, Response filed Nov. 9, 2018 to Non Final Office Action mailed Aug. 28, 2018", 15 pgs.
"U.S. Appl. No. 15/693,723, Corrected Notice of Allowability mailed May 13, 2019", 2 pgs.
"U.S. Appl. No. 15/693,723, Non Final Office Action mailed Nov. 30, 2018", 8 pgs.
"U.S. Appl. No. 15/693,723, Notice of Allowance mailed Mar. 15, 2019", 5 pgs.
"U.S. Appl. No. 15/693,723, PTO Response to Rule 312 Communication mailed Jun. 20, 2019", 2 pgs.
"U.S. Appl. No. 15/693,723, Response filed Feb. 8, 2019 to Non Final Office Action mailed Nov. 30, 2018", 7 pgs.
"U.S. Appl. No. 16/439,316, Non Final Office Action mailed Jun. 9, 2021", 5 pgs.
"U.S. Appl. No. 16/439,316, Notice of Allowance mailed Nov. 2, 2021", 7 pgs.
"U.S. Appl. No. 16/439,316, Preliminary Amendment Filed Jul. 12, 2019", 6 pgs.
"U.S. Appl. No. 16/439,316, Response filed Aug. 25, 2021 to Non Final Office Action mailed Jun. 9, 2021", 7 pgs.
"U.S. Appl. No. 16/687,171, Final Office Action mailed Jan. 7, 2022", 11 pgs.
"U.S. Appl. No. 16/687,171, Non Final Office Action mailed Sep. 24, 2021", 10 pgs.
"U.S. Appl. No. 16/687,171, Notice of Allowance mailed Mar. 30, 2022", 9 pgs.
"U.S. Appl. No. 16/687,171, Preliminary Amendment filed Mar. 10, 2020", 6 pgs.
"U.S. Appl. No. 16/687,171, Response filed Mar. 7, 2022 to Final Office Action mailed Jan. 7, 2022", 13 pgs.
"U.S. Appl. No. 16/687,171, Response filed Dec. 10, 2021 to Non Final Office Action mailed Sep. 24, 2021", 15 pgs.
"Chinese Application Serial No. 201680047010.8, Office Action mailed Mar. 17, 2020", (W/ English Translation), 21 pgs.
"Chinese Application Serial No. 201680047010.8, Office Action mailed Apr. 14, 2021", (W/ English Translation), 22 pgs.
"Chinese Application Serial No. 201680047010.8, Office Action mailed Sep. 29, 2020", (W/ English Translation), 18 pgs.
"Chinese Application Serial No. 201680047010.8, Response filed Jun. 5, 2020 to Office Action mailed Mar. 17, 2020", (W/ English Translation of Claims), 12 pgs.
"Chinese Application Serial No. 201680047010.8, Response filed Nov. 4, 2020 to Office Action mailed Sep. 29, 2020", (W/ English Translation of Claims), 12 pgs.
"European Application Serial No. 16732186.8, Response filed Sep. 3, 2018 to Office Action mailed Feb. 20, 2018", 16 pgs.
"European Application Serial No. 17771958.0, Response to Communication pursuant to Rules 161(1) and 162 EPC filed Nov. 18, 2019", 15 pgs.
"International Application Serial No. PCT/US2016/037765, International Preliminary Report on Patentability mailed Dec. 28, 2017", 10 pgs.
"International Application Serial No. PCT/US2016/037765, International Search Report mailed Nov. 21, 2016", 5 pgs.
"International Application Serial No. PCT/US2016/037765, Invitation to Pay Additional Fees and Partial Search Report mailed Sep. 9, 2016", 7 pgs.
"International Application Serial No. PCT/US2016/037765, Written Opinion mailed Nov. 21, 2016", 8 pgs.
"International Application Serial No. PCT/US2017/050957, International Preliminary Report on Patentability mailed Mar. 28, 2019", 12 pgs.
"International Application Serial No. PCT/US2017/050957, International Search Report mailed Jan. 24, 2018", 6 pgs.
"International Application Serial No. PCT/US2017/050957, Invitation to Pay Additional Fees and Partial Search Report mailed Nov. 21, 2017", 13 pgs.

(56) References Cited

OTHER PUBLICATIONS

"International Application Serial No. PCT/US2017/050957, Written Opinion mailed Jan. 24, 2018", 10 pgs.
"European Application Serial No. 16732186.8, Communication Pursuant to Article 94(3) EPC mailed Nov. 25, 2022", 7 pgs.
"European Application Serial No. 16732186.8, Response filed Apr. 4, 2023 to Communication Pursuant to Article 94(3) EPC mailed Nov. 25, 2022", 15 pgs.

\* cited by examiner

TIBIAL CUT GUIDE

CLAIM OF PRIORITY

This application is a continuation of U.S. patent application Ser. No. 16/687,171, filed Nov. 18, 2019, which is a continuation of U.S. patent application Ser. No. 15/184,016, filed on Jun. 16, 2016, now issued as U.S. Pat. No. 10,517,614, which claims the benefit of U.S. Provisional Patent Application Ser. No. 62/182,073, filed on Jun. 19, 2015, the benefit of priority of each of which is claimed hereby, and each of which is incorporated by reference herein in its entirety.

FIELD

The present subject matter relates to orthopedic procedures and, more particularly, to bone resection apparatuses and methods for performing knee arthroplasties.

BACKGROUND

Orthopedic procedures and prostheses are commonly utilized to repair and/or replace damaged bone and tissue in the human body. For example, a knee arthroplasty can be used to restore natural knee function by repairing damaged or diseased articular surfaces of the femur and/or tibia. An incision is made into the knee joint to expose the bones comprising the joint. Cut guides are used to guide the removal of the articular surfaces that are to be replaced. Prostheses are used to replicate the articular surfaces. Knee prostheses can include a femoral component implanted on the distal end of the femur, which articulates with a tibial component implanted on the proximal end of a tibia to replicate the function of a healthy natural knee. Various types of arthroplasties are known including a total knee arthroplasty, where all of the articulating compartments of the joint are repaired with prosthetic components, and a unicompartmental knee arthroplasty, where only one damaged compartment of the knee is repaired with prosthetic components.

Overview

The present inventors recognize, among other things, an opportunity for reducing surgical error and surgical complexity. More particularly, the present inventors have recognized that a component such as a pin or screw received in a cut guide can act as a cut stop to protect sensitive anatomical features that are desirable to maintain. Such features can include the intercondylar eminence and the anterior cruciate ligament (ACL) of the tibia. Furthermore, the present inventors have recognized that surgical complexity can be reduced by providing cut guides with a sagittal capture that predefines a sagittal cut. According to further examples, the present inventors recognize that the sagittal capture can be configured to provide a physician with various medial-lateral spaced options for the sagittal cut so the physician can set the cut guide in an appropriate location relative to the tibia such that the sagittal cut can be performed with minimal amounts of medial-lateral shilling of the cut guide relative to the tibia.

To further illustrate the apparatuses and methods disclosed herein, the following non-limiting examples are provided:

In Example 1, an apparatus for guiding a tibial bone cut during knee replacement surgery is disclosed. The apparatus can include a mounting portion configured to couple with an alignment mechanism, and a cutting portion connected to the mounting portion and defining a capture for a proximal cut, the cutting portion having an aperture disposed adjacent a first end of the capture.

In Example 2, the apparatus of Example 1, wherein the cutting portion can be offset from the mounting portion in at least one of a medial or lateral direction and the capture can be configured to define a medial-lateral cut length such that the proximal cut is to a single compartment of a knee.

In Example 3, the apparatus of Example 2, wherein the aperture can be disposed between the mounting portion and the capture.

In Example 4, the apparatus of any one or any combination of Examples 1-3, wherein the capture can communicate with the aperture.

In Example 5, the apparatus of any one or any combination of Examples 1-3, wherein the capture can terminate prior to the aperture.

In Example 6, the apparatus of any one or any combination of Examples 1-5, wherein the cutting portion can include a second capture for a sagittal cut.

In Example 7, the apparatus of Example 6, wherein at least a portion of the second capture can be defined by one or more projections extending proximally from a proximal surface of the cutting portion.

In Example 8, the apparatus of Example 7, wherein the one or more projections can taper toward the proximal surface from anterior to posterior.

In Example 9, the apparatus of Example 7, wherein the one or more projections can comprise a pair of medial-lateral spaced projections and the second capture can comprise three captures comprising a laterally disposed capture defined by a first surface of a first of the pair of projections, a medially disposed capture defined by a first surface of a second of the pair of projections, and a middle capture defined by a second surface of the first of the pair of projections and defined by a second surface of the second of the pair of projections.

In Example 10, the apparatus of Example 9, wherein the three captures can be spaced substantially 3 mm apart from one another in a medial-lateral direction.

In Example 11, the apparatus of any one or any combination of Examples 6 to 10 wherein the aperture can be disposed adjacent a first end of the second capture.

In Example 12, the apparatus of Example 11, wherein the aperture can be one of in communication with the second capture or spaced from the second capture.

In Example 13, the apparatus of any one or any combination of Examples 6 to 12, further comprising a component that can be configured to be received wherein the aperture, the component acting as a stop for one or both of the proximal cut and the sagittal cut.

In Example 14, the apparatus of any one or any combination of the preceding Examples, wherein the mounting portion can include a slot configured to receive a fastener, the slot configured to allow for proximal-distal adjustment of the apparatus relative to the knee, the mounting portion having indicia disposed adjacent the slot for referencing movement of the apparatus relative to the fastener.

In Example 15, the apparatus of any one or any combination of the preceding Examples, can further comprise a second mounting portion having a plurality of mounting holes therethrough, at least one of the mounting holes arranged substantially parallel with the aperture and at least a second of the mounting holes arranged oblique to the aperture.

In Example 16, an apparatus for guiding a tibial bone cut during knee replacement surgery is disclosed. The apparatus can include a mounting portion configured to couple with an alignment mechanism, and a cutting portion connected to the mounting portion and defining a first capture for a proximal cut and a second capture for a sagittal cut.

In Example 17, the apparatus of Example 16, wherein the cutting portion can have an aperture disposed between the first capture and the second capture.

In Example 18, the apparatus of Example 17, wherein the first capture can be offset from the second capture and the aperture is disposed adjacent a first end of the first capture and adjacent a first end of the second capture.

In Example 19, the apparatus of Example 18, wherein the aperture can at least be one of in communication with the first capture, spaced from the first capture, in communication with the second capture, or spaced from the second capture.

In Example 20, the apparatus of any one or any combination of Examples 16 to 19, wherein at least a portion of the second capture is defined by one or more projections extending proximally from a proximal surface of the cutting portion.

In Example 21, the apparatus of Example 20, wherein the one or more projections can define a plurality of locations for the sagittal cut.

In Example 22, the apparatus of Example 20, wherein the one or more projections can comprise a pair of medial-lateral spaced projections and the second capture can comprise three captures comprising a laterally disposed capture defined by a first surface of a first of the pair of projections, a medially disposed capture defined by a first surface of a second of the pair of projections, and a middle capture defined by a second surface of the first of the pair of projections and defined by a second surface of the second of the pair of projections.

In Example 23, the apparatus of Example 22, wherein the three captures are spaced substantially 3 mm apart from one another in a medial-lateral direction.

In Example 24, the apparatus of any one or any combination of Examples 17 to 23, can further comprise a component configured to be received within the aperture, the component acting as a stop for one or both of the proximal cut and the sagittal cut.

In Example 25, the apparatus of any one or any combination of Examples 17 to 24, can further comprise a stylus assembly configured to be received in the first capture and mountable therein in a first position and a second position, wherein in the first position the stylus assembly includes a first tip configured to reference the first capture a predetermined distance from an anatomical landmark, and wherein in the second position the stylus assembly includes a second tip configured to reference the first capture a second predetermined distance from the anatomical landmark.

In Example 26, a method of performing a tibial knee resection is disclosed. The method can include mounting a cut guide to an alignment mechanism, the cut guide configured to facilitate one or both of a proximal cut and a sagittal cut, adjusting a position of the guide with reference to one or more anatomical landmarks of the knee, fixating the cut guide to the tibia using a slot that is configured to allow for proximal-distal adjustment of the guide relative to the tibia, inserting a stop into the cut guide to limit one or both of the proximal cut and the sagittal cut, and resecting the tibia by performing one or both of the proximal cut and the tibia cut utilizing the cut guide.

In Example 27, the method of Example 26, wherein the stop can comprise one of a bone screw or pin.

In Example 28, the method of any one or any combination of Examples 26 and 27, wherein the anatomical landmarks can include one or more of the intercondylar eminence of the tibia, a connection position of an ACL with the tibia, a medial third of a tubercle at insertion of a PCL, and an intercondylar geometry of a femur.

In Example 29, the method of any one or any combination of Examples 26 to 28, can further comprise removing the cut guide and repeating the method of Example 24 with a second cut guide for resecting a second compartment of the knee.

In Example 30, the method of any one or any combination of Examples 26 to 29, wherein at least one of the cut guide and second cut guide can be configured to facilitate the sagittal cut in any one of a plurality of medial-lateral spaced locations.

In Example 31, the method of any one or any combination of Examples 26 to 30, can further comprise mounting a stylus assembly to one or more of the cut guide and the second cut guide, and referencing an anatomical landmark with a stylus to set a proximal-distal height of the cut guide relative to the tibia.

In Example 32, the apparatuses or method of any one or any combination of Examples 1-31 can optionally be configured such that all elements or options recited are available to use or select from.

These and other examples and features of the present apparatuses and methods will be set forth in part in the following Detailed Description. This Overview is intended to provide non-limiting examples of the present subject matter—it is not intended to provide an exclusive or exhaustive explanation. The Detailed Description below is included to provide further information about the present apparatuses and methods.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

DETAILED DESCRIPTION

The present application relates to devices and methods that can be used in a unicompartmental knee replacement procedure, a bicompartmental knee replacement procedure comprised of two unicompartmental knee replacements, a procedure that utilizes a single (total) femoral component and two unicompartmental tibial components, and other types of knee replacement procedures. The disclosed devices include tibial cut guides having a mounting portion configured to couple with an alignment mechanism and a cutting portion connected to the mounting portion. According to some examples, the cutting portion can define a capture for a proximal cut and can have an aperture disposed adjacent a first end of the capture. According to further examples, the cutting portion can include a second capture for a sagittal cut.

Figure 1A:
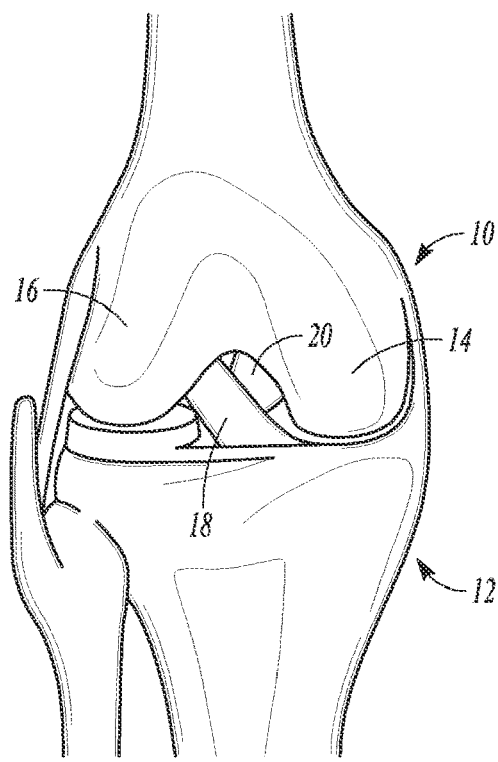
FIG. 1A is an anterior view of a natural femur and tibia according to example of the present application.
Figure 1B:
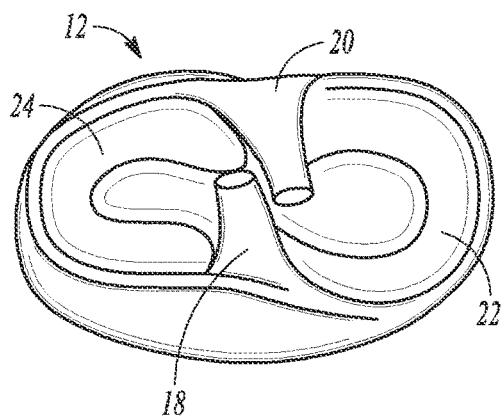
FIG. 1B is a top view of the tibia of FIG. 1A according to example of the present application.

FIG. 1A illustrates a natural femur 10 and tibia 12. The femur 10 can include medial 14 and lateral 16 condyles at a distal end of the femur 10. Various ligaments can be attached to the femur 10 and/or the tibia 12. An anterior cruciate ligament (ACL) 18 can extend from an anterior side of the tibia 12 to the femur 10, and a posterior cruciate ligament (PCL) 20 can extend from a posterior side of the tibia 12 to the femur 10. FIG. 1B is a top view of the tibia 12 and further illustrates some of these ligaments as well as a medial meniscus 22 and a lateral meniscus 24 that are located between the tibia 12 and the medial 14 and lateral 16 condyles.

Figure 1C:
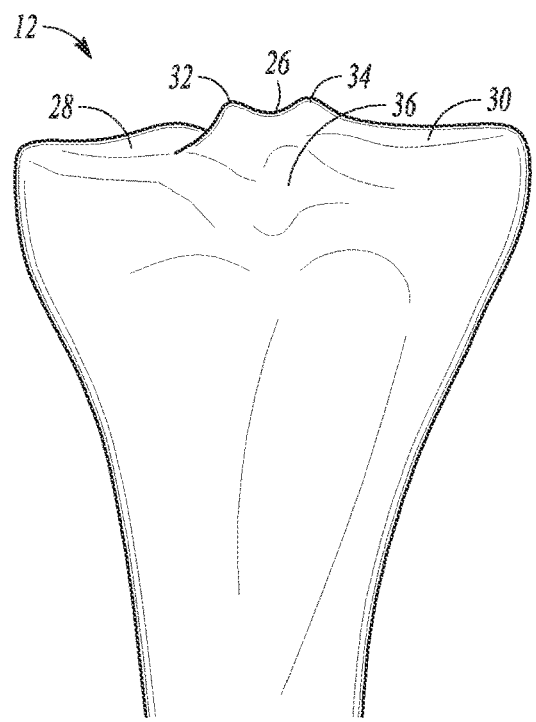
FIG. 1C is an anterior view of the tibia of FIGS. 1A and 1B, with the anatomical features shown in FIG. 1B removed according to example of the present application.

FIG. 1C illustrates a posterior side view of the tibia 12 with the ligaments and other anatomical features shown in FIG. 1B removed. The tibia 12 can include an intercondylar eminence 26, which is a bony elevation or raised area between a medial articular surface 28 and a lateral articular surface 30 at a proximal end of the tibia 12. The intercondylar eminence 26 can include medial 32 and lateral 34 tubercles extending from the intercondylar eminence 26. The ACL 18 and PCL 20 are attached to the tibia 12 at locations anterior and posterior, respectively, to the intercondylar eminence 26. For reference, the PCL 20 is attached to the tibia 12 at a location 36 on a posterior end of the tibia 12.

In a unicompartmental knee replacement procedure (sometimes referred to as a "unicondylar" knee replacement procedure or simply a "UKA") one of the medial 14 and lateral 16 condyles of the femur 10 is resected. Similarly, the tibia 12 is resected to remove one of the medial articular surface 28 and the lateral articular surface 30 using a cutting apparatus such as those disclosed herein. More particularly, femoral cutting apparatuses can be utilized to remove corresponding articular surfaces of the femur 10 that would otherwise interface with either the medial articular surface 28 or the lateral articular surface 30. Prostheses would be implanted on the femur 10 and the tibia 12 providing for the replaced articular surfaces. Other portions of the knee, e.g., the intercondylar eminence 26, ACL 18, and PCL 20 would be maintained in the UKA. In a bicompartmental knee replacement procedure, both the medial 14 and lateral 16 condyles of the femur 10 are resected and the tibia 12 is resected to remove the medial articular surface 28 and the lateral articular surface 30. Such resection of the tibia 12 can be performed using a cutting apparatus as disclosed herein. Similar to a unicompartmental knee replacement procedure, the bicompartmental knee replacement procedure maintains portions of the knee such as the intercondylar eminence 26. Similarly, a knee replacement procedure that would utilize a total femoral component and two unicompartmental tibial components can seek to maintain portions of the knee such as the intercondylar eminence 26.

As used herein, "proximal" refers to a direction generally toward the torso of a patient, and "distal" refers to the opposite direction of proximal, i.e., away from the torso of a patient. "Anterior" refers to a direction generally facing away from the patient, i.e. toward the surgeon performing the surgery, and "posterior" refers to the opposite direction of anterior, i.e., toward the front (anterior) of a patient or knee. In the context of cutting apparatus such as those disclosed herein, such directions correspond to the orientation of the apparatus when in use (i.e. when mounted to or adjacent the patient in an operable position to make desired resections), such that a proximal portion of the cutting apparatus is that portion which will ordinarily be closest to the torso of the patient, the anterior portion closest to the surgeon, the posterior portion generally closest to the anterior portion of the patient's knee, etc.

Figure 2:
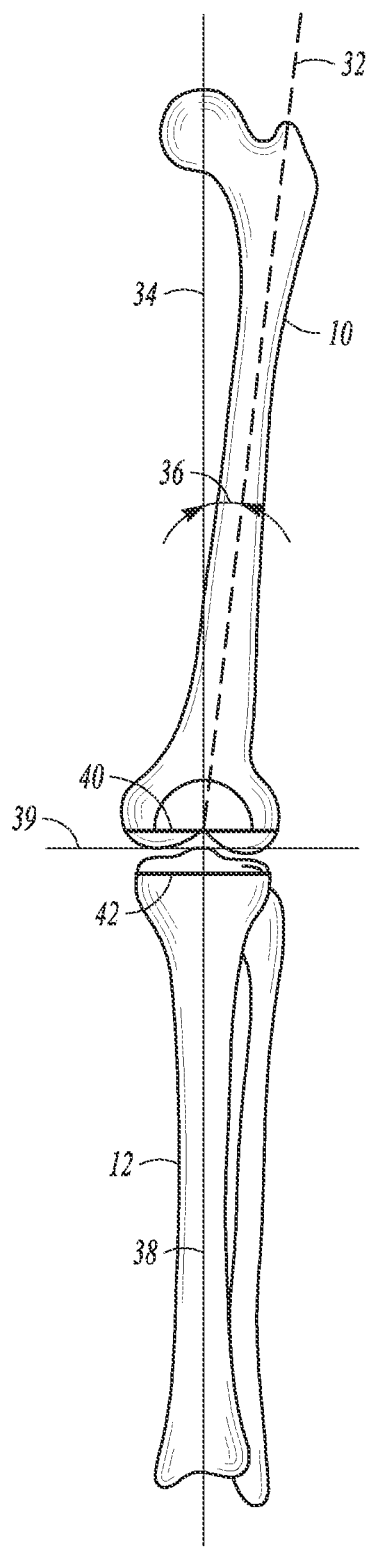
FIG. 2 is a front elevation view of a tibia and a femur showing axes of the knee joint according to example of the present application.
Figure 3:
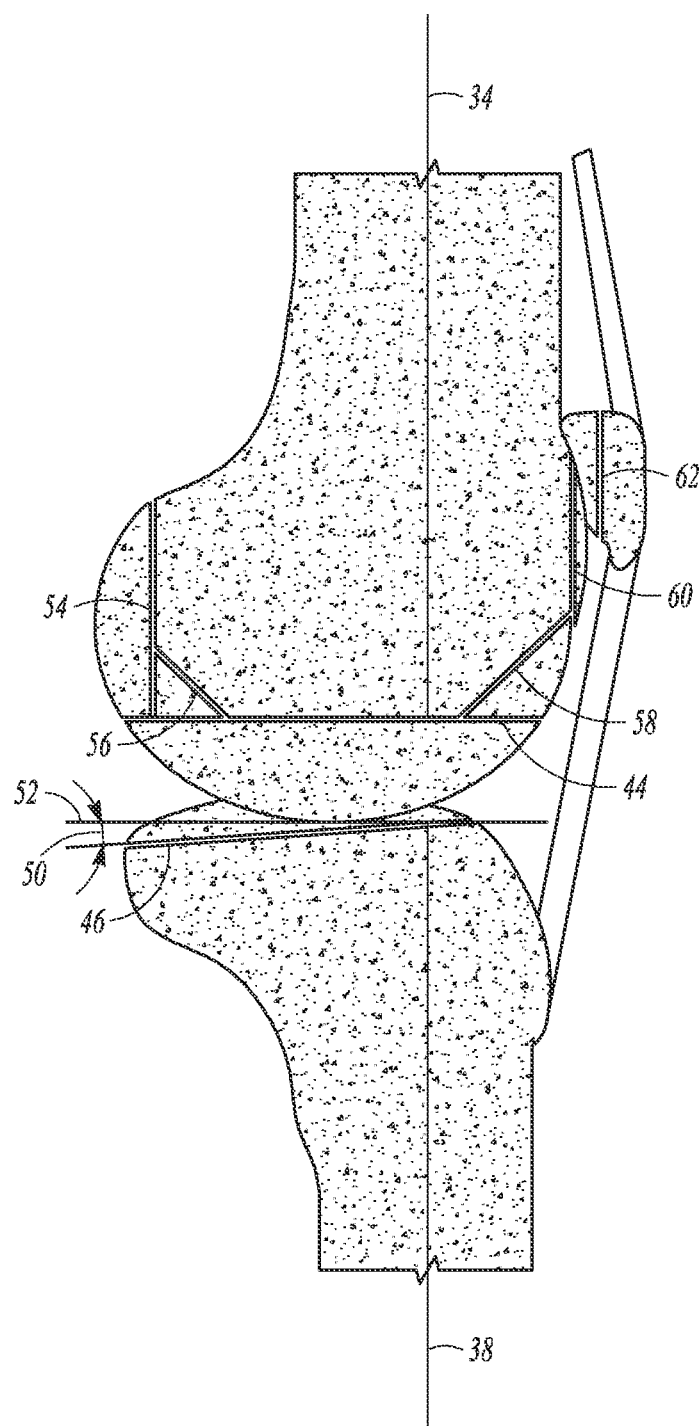
FIG. 3 is a side section view of a knee joint showing typical bone cuts used in replacing the joint surfaces according to example of the present application.
Figure 4:
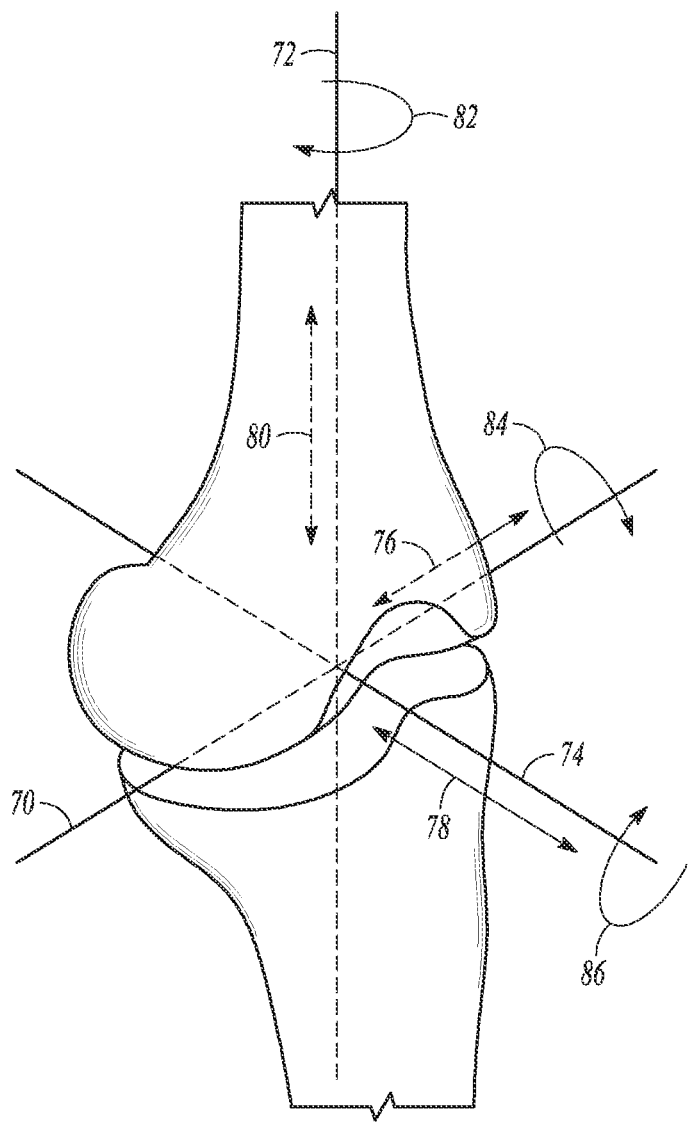
FIG. 4 is a perspective view of knee joint showing aspects of component positioning according to example of the present application.

FIGS. 2-4 illustrate several aspects of implant orientation. FIG. 2 illustrates various axes of the lower limb in the frontal plane. Axes can be defined for each segment of the lower limb. For example, the femur 10 has an anatomic axis 32 coinciding generally with its intramedullary canal. It also has a mechanical axis 34, or load axis, running from the center of the femoral head to the center of the knee. The angle 36 between these two axes 32, 34 in the frontal plane varies within the patient population but is on the order of 4-9°. The two axes 32, 34 are approximately superimposed in the sagittal plane (FIG. 3). Likewise, the tibia 12 has a mechanical axis 38 coinciding generally with its intramedullary canal. The mechanical axis 38 of the tibia 12 runs from the center of the knee to the center of the ankle. The transverse axis, or joint line 38, about which the knee flexes, is parallel to a line through the medial and lateral femoral condyles and parallel to the tibial plateau. Typically, the distal femur and proximal tibia are resected to be parallel to the joint line 39, and thus perpendicular to the mechanical axes 34, 38 as indicated at 40 and 42. The intersection of the femoral and tibial mechanical axes 34, 38 may subtend a small angle relative to one another. However, the angle can be small such that the axes 34, 38 are approximately collinear and may be treated as collinear for most purposes.

FIG. 3 illustrates the knee joint from the side or sagittal view and various bone cuts that may be made to align implant components. The distal femoral cut 44 is typically made perpendicular to the femoral axes 32, 34 in the sagittal plane. The proximal tibial resection 46 is typically cut to match the natural posterior slope, or rotation, of the proximal tibia relative to the mechanical axes 34, 38. The amount of posterior to anterior slope 50 relative to a reference line 52 perpendicular to the mechanical axes 34, 38 varies in the patient population but is on the order of 5° to 7°. The distance between the distal femoral cut 44 and proximal tibial cut 46 along the mechanical axes 34, 38 is the extension gap. Other cuts may be made depending on the components that are to be implanted. These include a posterior femoral cut 54, posterior femoral chamfer cut 56, anterior femoral chamfer cut 58, anterior femoral cut 60, and a tibial sagittal cut (not shown in FIG. 3). The patella 62 may also be cut to allow for replacement of the patellar articular surface.

As described above, in a unicompartmental knee replacement procedure, only the medial or lateral side of the knee joint is resurfaced. Furthermore, the trochlear, or patellar bearing, surface of the femur is typically left intact. Unicompartmental implant designs vary, but typically only the distal femoral cut 44, the posterior femoral chamfer cut 56 and the posterior femoral cut 54 are needed to accommodate the unicompartmental femoral implant.

FIG. 4 depicts six aspects of component positioning relative to a coordinate system in which the x-axis 70 corresponds approximately to the joint line 39, the z-axis 72 corresponds approximately to the mechanical axes 34 and 38, and the y-axis 74 is normal to the other two. Position along each of these axes is depicted by arrows. Position along the x, y, and z axes determines the medial/lateral (dx) 76, anterior/posterior (dy) 78, and proximal/distal (dz) 80 positioning of components respectively. Rotation about each of these axes is also depicted by arrows. Rotation about the z-axis (rz) 82 corresponds anatomically to external rotation of the femoral component, rotation about the x-axis (rx) 84 corresponds to extension plane rotation, and rotation about the y-axis (ry) 86 corresponds to varus/valgus rotation.

Figure 5:
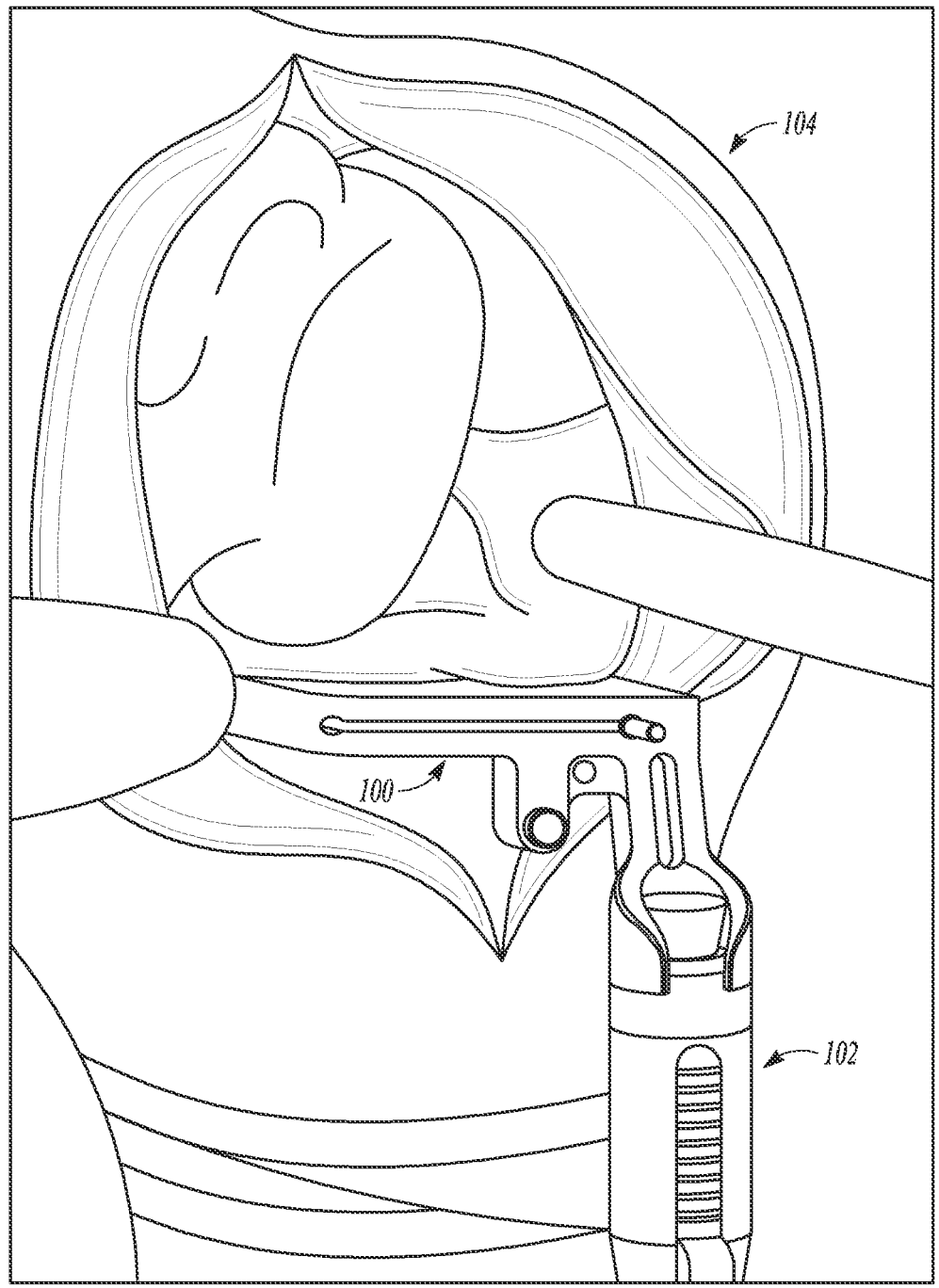
FIG. 5 is a perspective view of a knee of a patient having a cut guide mounted thereto according to an example of the present application.
Figure 5A:
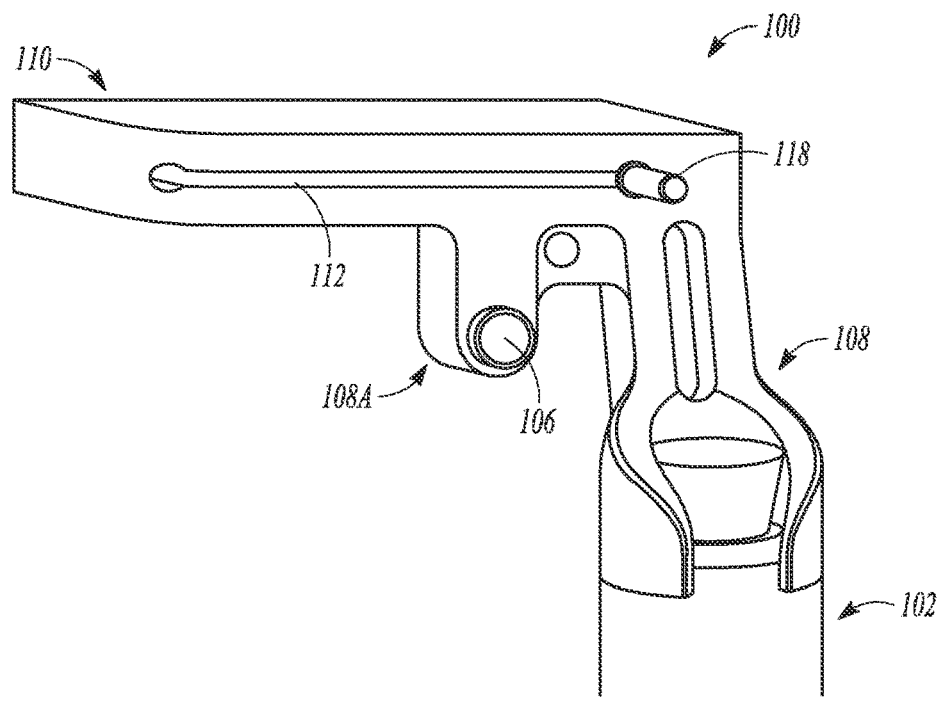
FIG. 5A is an enlarged view of the cut guide of FIG. 5 according to example of the present application.

FIG. 5 shows a tibial cut guide 100 mounted to an alignment mechanism 102 according to an example embodiment. FIG. 5A shows an enlargement of the tibial cut guide 100. As shown in FIG. 5A, the tibial cut guide 100 can be fixated to a knee 104 of a patient by a fastener 106. The tibial guide 100 can include a mounting portion 108 and a cutting portion 110. The cutting portion 110 can include a capture 112.

The tibial cut guide 100 of FIGS. 5 and 5A can be configured for resecting a single compartment of the tibia. As such, the tibial cut guide 100 can be utilized to perform a unicompartmental knee replacement procedure or a bicompartmental knee replacement procedure comprised of two unicompartmental knee replacements. Therefore, the capture 112 can be configured to define a medial-lateral cut length such that the proximal cut to the tibia is to a single compartment of the knee 104 (FIG. 5).

FIG. 5A illustrates the mounting portion 108 can be configured to couple with an alignment mechanism 102. The construction of the alignment mechanism 102 is described in United States Application Publication 2013/0204260, the entire disclosure of which is incorporated herein by reference. FIG. 5A illustrates that the mounting portion 108 can include a second mounting portion 108A, which can be configured with apertures, slots, or other mechanisms that allow the tibial cut guide 100 to be fixated to the knee 104 (FIG. 5) by fasteners including the fastener 106.

As is best illustrated in FIG. 5A, the mounting portion 108 can extend distally from and can be connected to the cutting portion 110. A posterior surface of the cutting portion 110 can be configured to interface with an anterior portion of the knee 104. The capture 112 extends through the cutting portion 110 generally from the anterior thereof to the posterior. According to the illustrated examples the cutting portion 110 can be offset a medial-lateral distance as well as a proximal-distal distance from the mounting portion 108.

As best illustrated in FIG. 5A the cutting portion 110 can be configured to receive a stop component 118 such as a pin, screw or other fastener therein. The stop component 118 can be positioned adjacent a first end of the capture 112. Unless otherwise indicated herein, the term "adjacent" can mean that the referenced features are both spaced from, in contact with, and/or in communication with one another. The stop component 118 can act to limit travel of a saw performing resection of the knee 104. Thus, sensitive areas such as the intercondylar eminence and/or the posterior cruciate ligament (PCL) can be spared contact with the saw during the proximal and/or sagittal resection allowing them to be better preserved.

Figure 6:
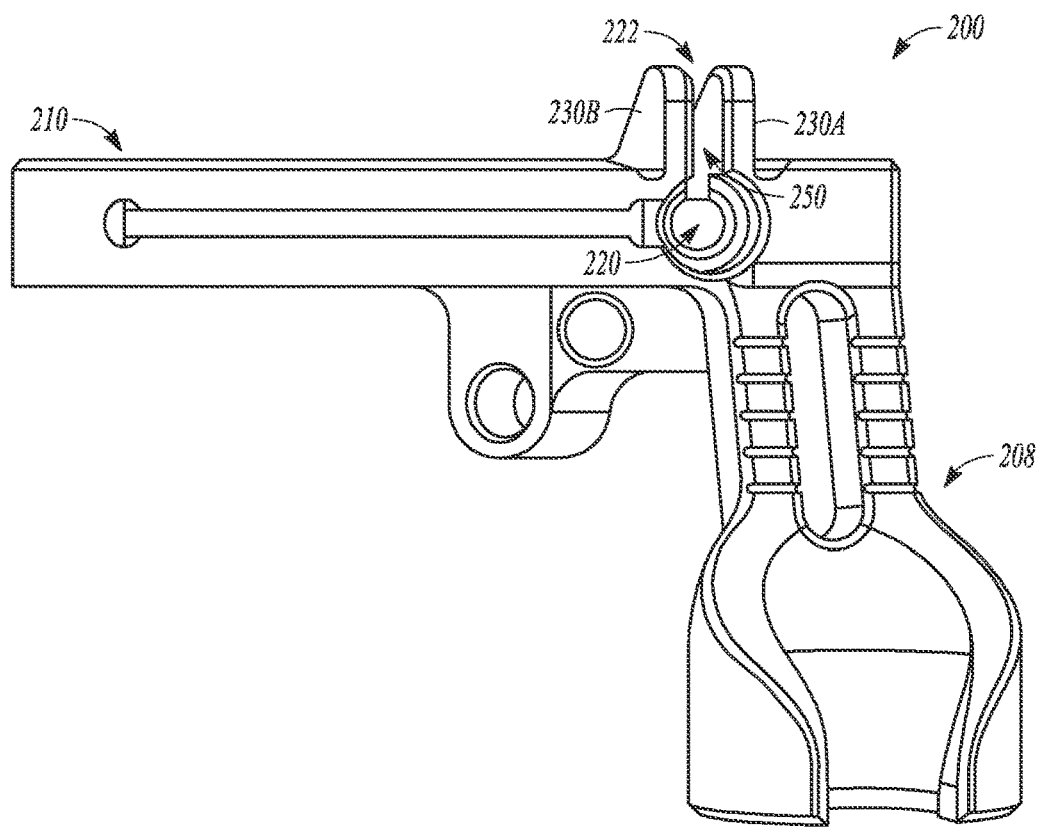
FIG. 6 is a perspective view of another example of a cut guide having a sagittal cut mechanism according to example of the present application.
Figure 6A:
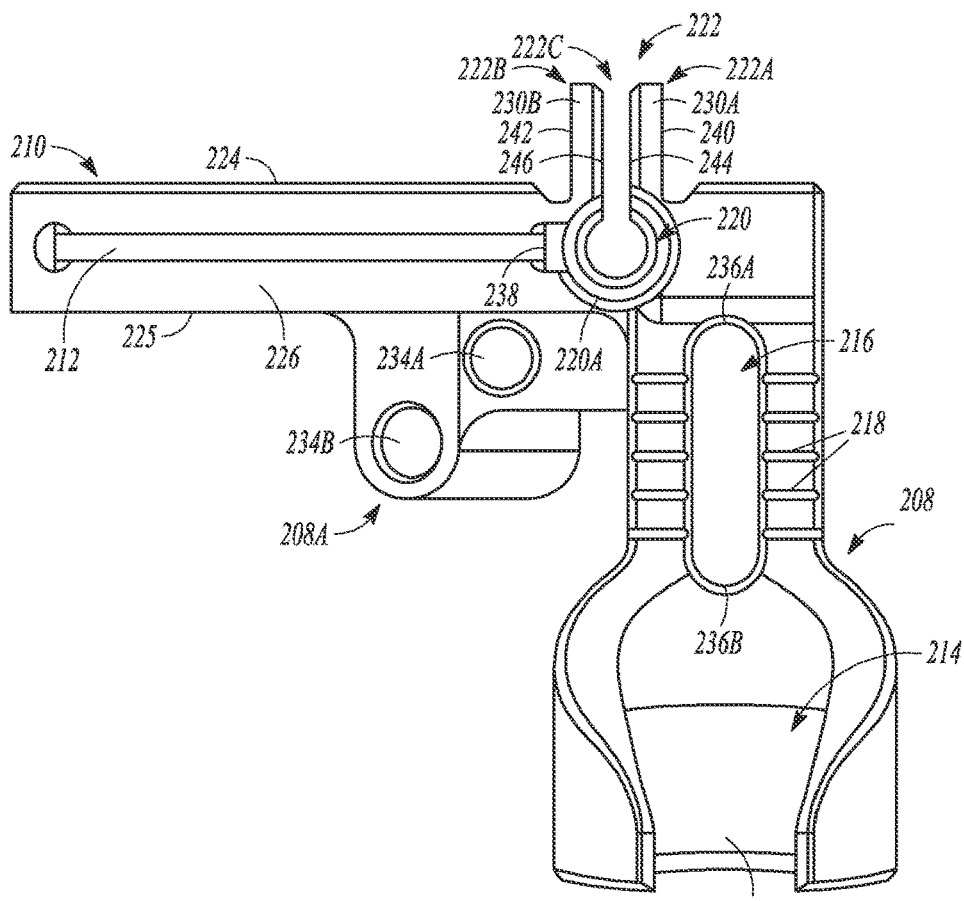
FIG. 6A is a plan view of an anterior side of the cut guide of FIG. 6 according to example of the present application.
Figure 6B:
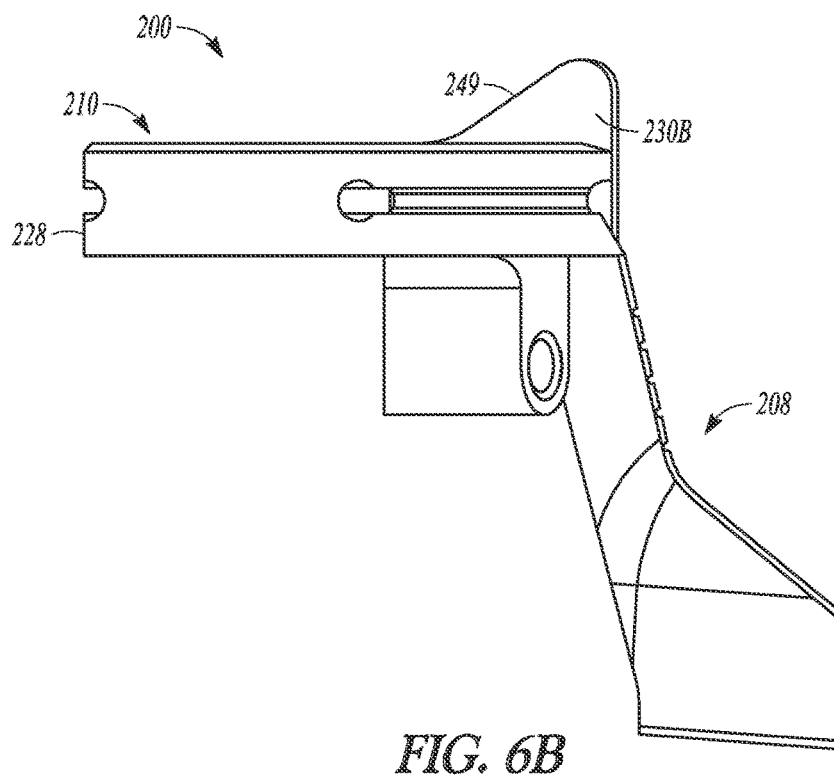
FIG. 6B is a plan view of a first side of the cut guide of FIG. 6 according to example of the present application.
Figure 6C:
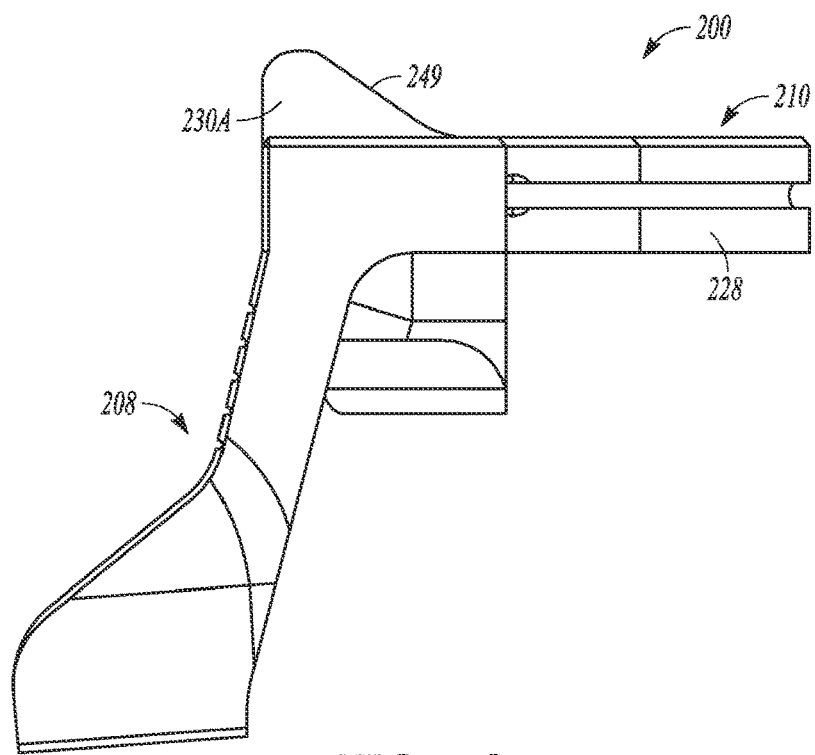
FIG. 6C is a plan view of a second side of the cut guide of FIG. 6 according to example of the present application.
Figure 6D:
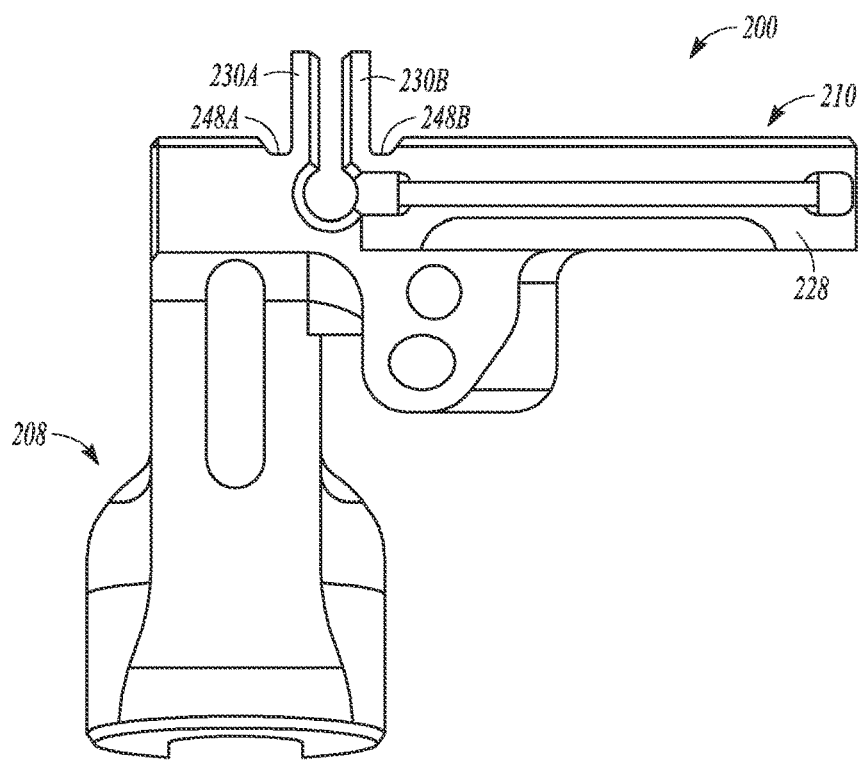
FIG. 6D is a plan view of a posterior side of the cut guide of FIG. 6 according to example of the present application.
Figure 6E:
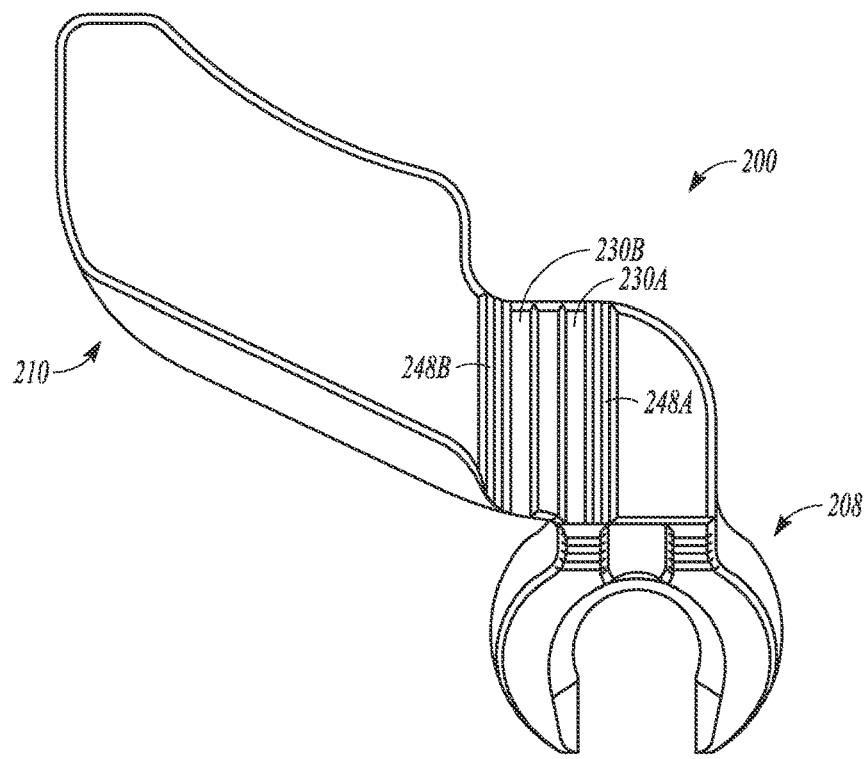
FIG. 6E is a plan view of a proximal side of the cut guide of FIG. 6 according to example of the present application.
Figure 6F:
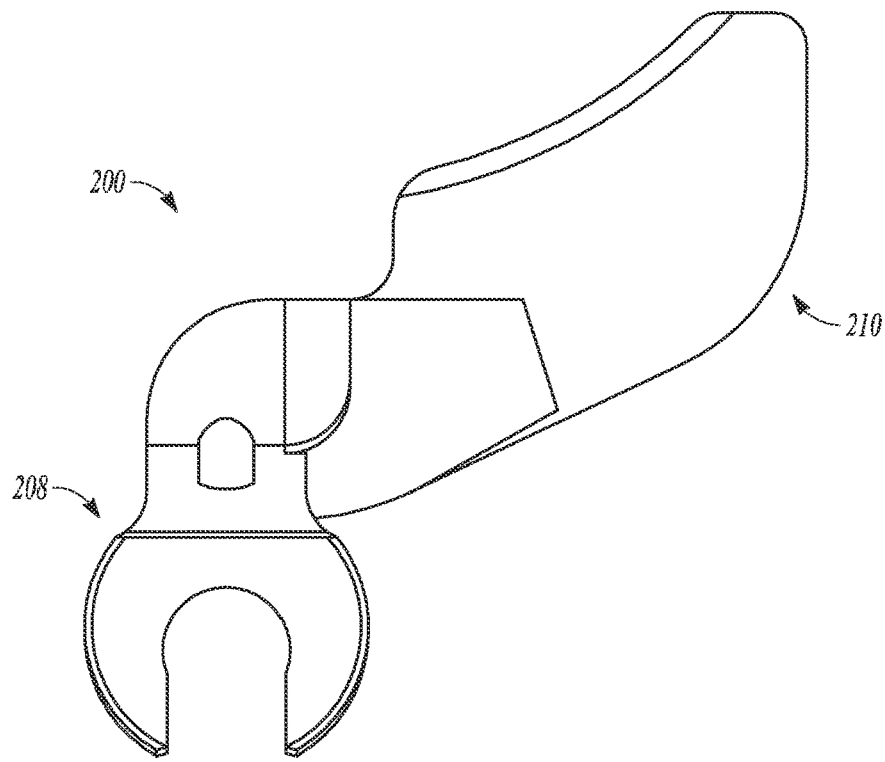
FIG. 6F is a plan view of a distal side of the cut guide of FIG. 6 according to example of the present application.

FIGS. 6 to 6F illustrate a cut guide 200 according to another example. Similar to the example of FIGS. 5 and 5A, the cut guide 200 can include a mounting portion 208 and a cutting portion 210. As shown in FIG. 6A, the mounting portion 208 can include a second mounting portion 208A, a receptacle 214, a slot 216, and indicia 218. As shown in FIG. 6A, the cutting portion 210 can include a capture 212 for the proximal cut, an aperture 220, a second capture 222 for a sagittal cut, a proximal surface 224, a distal surface 225, an anterior surface 226, and a posterior surface 228 (FIGS. 6B, 6C, and 6D). According to the example of FIG. 6A the second capture 222 can include projections 230A and 230B.

In the examples of FIGS. 6 to 6F, the mounting portion 208 can be configured to couple with an alignment mechanism (not shown) as described previously. In particular, the receptacle 214 can be provided to receive an end portion of the alignment mechanism along a tapered inner surface 232 (FIG. 6A). The second mounting portion 208A can be disposed distal of the cutting portion 210 and can be connected to the mounting portion 208. According to the illustrated example, the second mounting portion 208A can include a plurality of holes 234A and 234B extending therethrough. The hole 234A can extend anterior-posterior in a manner generally parallel with the aperture 220 of the cutting portion 210. The hole 234B can be arranged at an angle (e.g., oblique) to the aperture 220 such that the hole 234B extends both anterior-posterior as well as medial-lateral.

The slot 216 can extend through the mounting portion 208 and can extend generally parallel with the aperture 220 of the cutting portion 210 (e.g., can have a generally anterior-posterior extent). The slot 216 can also extend proximal-distal from a first end 236A to a second end 236B. The slot 216 can be configured to receive a fastener (not shown) and can allow for proximal-distal adjustment of the tibial cut guide 200 relative to the knee. The indicia 218 can be disposed adjacent the slot 216 along an anterior surface of the mounting portion 208 for referencing movement of the tibial cut guide 200 relative to the fastener and knee.

The cutting portion 210 can be connected to the mounting portion 208 (e.g., integral therewith so as to comprise a single component). As previously described, the cutting portion 210 defines the capture 212 (e.g., a slot) for the proximal cut. The cutting portion 210 can also have the aperture 220 disposed adjacent a first end 238 of the capture 212. The aperture 220 can extend generally anterior-posterior while the capture 212 can extend both anterior-posterior and proximal-distal (e.g. the capture 212 can be defined to have a small degree of distal down angle from the anterior to posterior). As illustrated in FIG. 6A, the cutting portion 210 around the aperture 220 can form a counterbore 220A configured to receive a head of the stop component (e.g., stop component 118 of FIGS. 5 and 5A) therein. The counterbore 220A can be contacted by the head to aid in holding the cut guide 200 against the knee.

As discussed previously, the aperture 220 is configured to receive the stop component, which can act to limit travel of the saw performing resection of the knee. Thus, sensitive areas such as the intercondylar eminence and/or the posterior cruciate ligament (PCL) can be spared contact with the saw during the proximal and/or sagittal resection allowing them to be better preserved.

According to examples, the cutting portion 210 can be offset from the mounting portion 208 in one of a medial or lateral direction. As shown in FIG. 6A the cut guide 200 comprises a medial cut guide, and thus, the cutting portion 210 is offset in both the medial direction and the proximal direction from the mounting portion 208. The capture 212 can be spaced from the proximal surface 224 and can extend from the anterior surface 226 to the posterior surface 228. The capture 212 can be configured to define a medial-lateral cut length such that the proximal cut is to a single compartment of a knee. The aperture 220 can be disposed between the mounting portion 208 and the capture 212. According to some examples such as the example of FIGS. 6 to 6F, the capture 212 can terminate prior to the aperture 220 (i.e. be spaced therefrom by a portion of the cutting portion 210). However, in other examples (e.g., FIG. 8) the capture can communicate with the aperture.

The example of FIGS. 6 to 6F illustrates the second capture 222 for the sagittal cut. At least a portion of the second capture 222 is defined by the projections 230A and 230B extending proximally from the proximal surface 224 of the cutting portion 210. The projections 230A and 230B can comprise a pair of medial-lateral spaced projections as illustrated, but can comprise a single projection, or three or more projections as desired according to other examples. With the pair of projections 230A and 230B, the second capture 222 can comprise three captures 222A, 222B, and 222C (FIG. 6A). Similarly, if a single projection is utilized the second capture 222 would comprise two captures. Thus, the number of captures can be n+1 with respect to the number of projections utilized by the cut guide.

According to FIG. 6A, the laterally disposed sagittal capture 222A can be defined by a first surface 240 of the first projection 230A of the pair of projections 230A, 230B. Similarly, the medially disposed sagittal capture 222B can be defined by a first surface 242 of the second projection 230B of the pair of projections 230A, 230B. The middle sagittal capture 222C can be defined by a second surface 244 of the first projection 230A and defined by a second surface 246 of the second projection 230B, According to one example, each projection 230A, 230B can have a medial-lateral length of substantially 3 mm such that the three captures 222A, 222B, and 222C are spaced substantially 3 mm apart from one another in the medial-lateral direction. Grooves 248A and 248B (FIGS. 6D, and 6E) can be formed in the proximal surface 224 adjacent the projections 230A and 230B. The projections 230A and 230B can taper 249 toward the proximal surface 224 from anterior to posterior as illustrated in FIGS. 6B and 6C. In some examples, the aperture 220 can be disposed adjacent a first end 250 (FIG. 6) of the second capture 222 (e.g., the end of the middle sagittal capture 222C of FIG. 6A). As shown in FIGS. 6 and 6A the aperture 220 is in communication with the second capture 222. However, in other examples, the aperture 220 is spaced from the second capture 222 (e.g., can have a part of the cutting portion 210 disposed between the aperture 220 and the second capture 222).

During use, the cut guide 200 can be initially mounted to the alignment mechanism (e.g., the alignment mechanism 102 of FIG. 5). As discussed, the cut guide 200 can be configured to facilitate one or both of a proximal cut and a sagittal cut. The position of the cut guide 200 can be adjusted with reference to one or more anatomical landmarks of the knee. For example, with regard to the proximal cut the physician can utilize a stylus assembly (See FIGS. 9-10) mounted to the cut guide 200 to reference an anatomical landmark (e.g., one of the un-resected medial articular surface 28 (FIG. 1C) and/or the un-resected lateral articular surface 30 (FIG. 1C)) to set a proximal-distal height of the cut guide relative to the tibia. Further proximal-distal adjustment can be performed as desired utilizing the indicia 218 and slot 216 once the cut guide 200 is fixated to the knee. In particular, the cut guide 200 can be fixated to the tibia using the slot 216 that is configured to allow for proximal-distal adjustment of the guide 200 relative to the tibia. Thus, further proximal-distal adjustment can be performed as desired utilizing the slot 216 and referencing the indicia 218 once the cut guide 200 is fixated to the knee. With regard to the sagittal cut, the physician can reference anatomical landmarks such as the connection position of the ACL with the tibia and/or the intercondylar eminence 26 (FIG. 1C) to set a medial-lateral position, a medial third of the tubercle at insertion of the PCL, and/or an intercondylar geometry of the femur to set a proximal-distal position.

According to some examples, a stop (e.g., the stop component 118 of FIGS. 5 and 5A) can be inserted in to the cut guide 200 to limit one or both of the proximal cut and the sagittal cut. According to some examples, the stop can comprise a screw used to fixate the guide to the tibia. The tibia can be resected by performing one or both of the proximal cut and the tibia cut utilizing the cut guide 200. According to further examples such as for a bicompartmental knee procedure, the cut guide can be removed and the afore described process can be repeated with a second cut guide for resecting a second compartment of the knee. The second cut guide (e.g., a lateral cut guide) can have a design similar to the medial cut guide 200 of FIGS. 6 to 6F. At least one of the cut guide and the second cut guide can be configured to facilitate the sagittal cut in any one of a plurality of medial-lateral spaced locations. However, in other examples the second cut guide may differ in construction (e.g., lack a sagittal capture, etc.) from that of the first cut guide.

Figure 7:
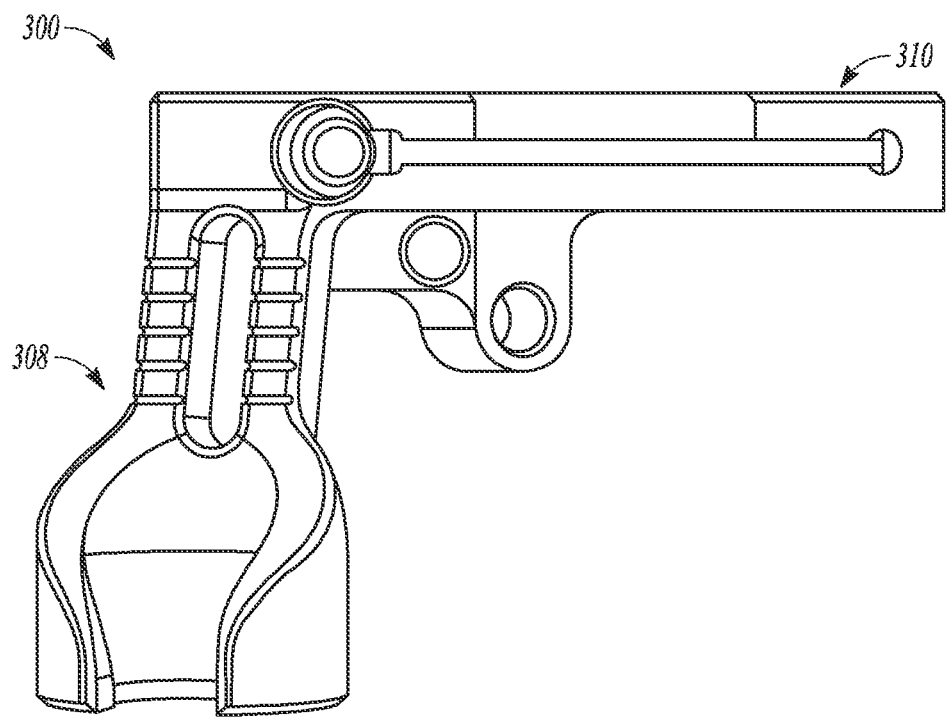
FIG. 7 is a perspective view of another example of a cut guide according to example of the present application.
Figure 7A:
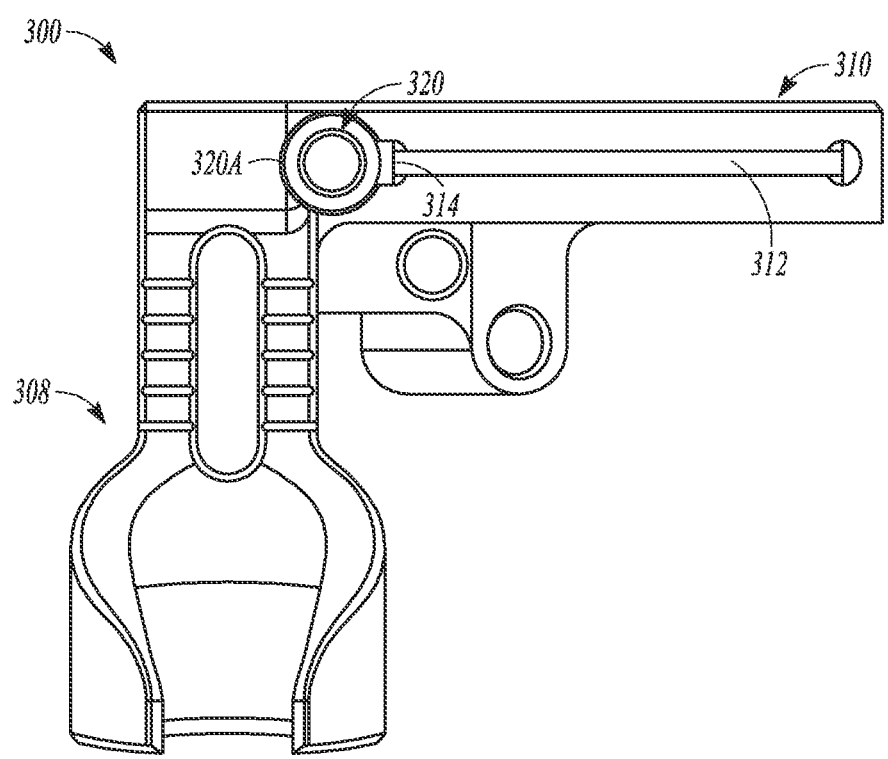
FIG. 7A is a plan view of an anterior side of the cut guide of FIG. 7 according to example of the present application.
Figure 7B:
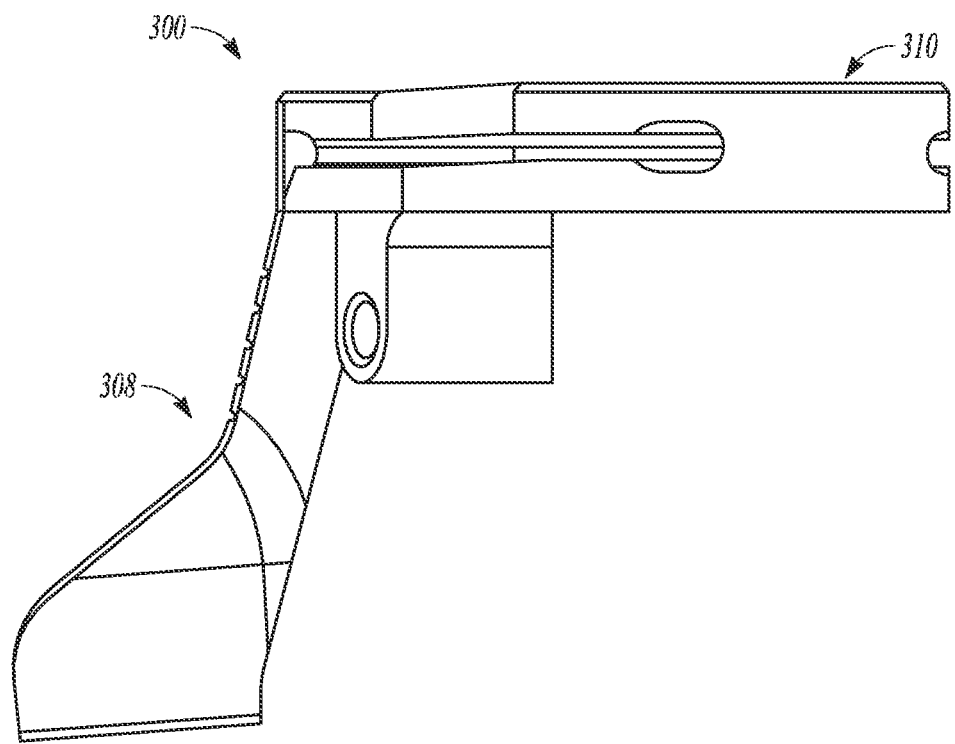
FIG. 7B is a plan view of a first side of the cut guide of FIG. 7 according to example of the present application.
Figure 7C:
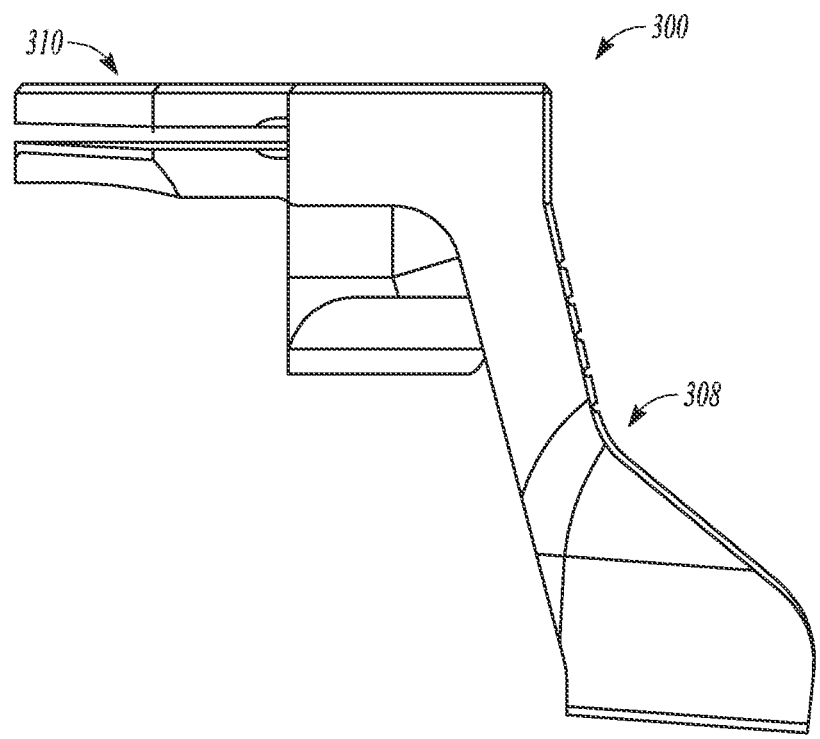
FIG. 7C is a plan view of a second side of the cut guide of FIG. 7 according to example of the present application.
Figure 7D:
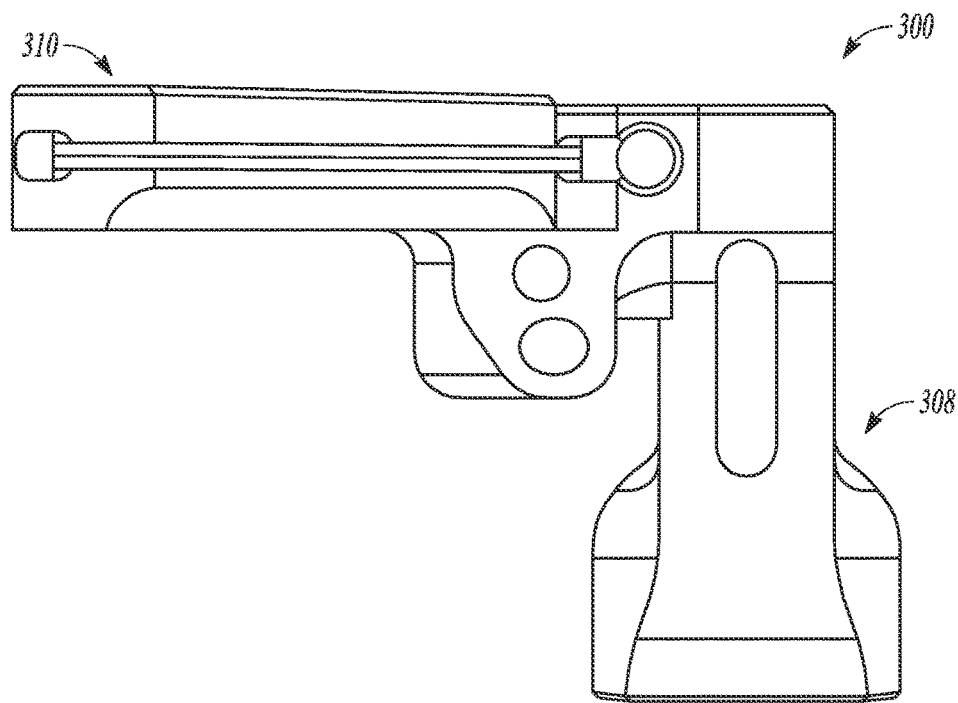
FIG. 7D is a plan view of a posterior side of the cut guide of FIG. 7 according to example of the present application.
Figure 7E:
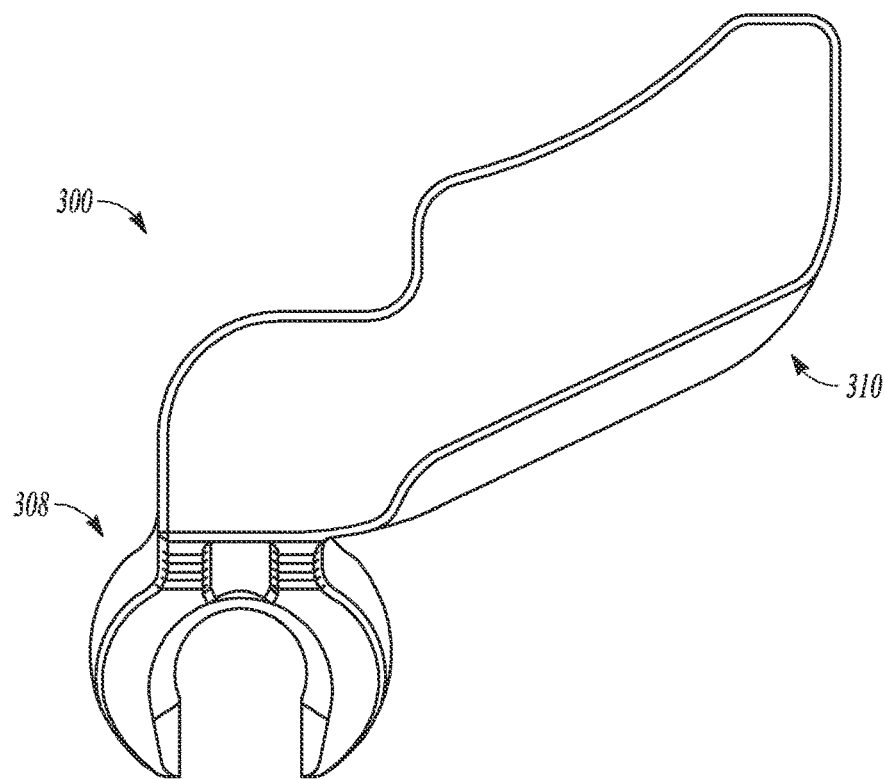
FIG. 7E is a plan view of a proximal side of flee cut guide of FIG. 7 according to example of the present application.
Figure 7F:
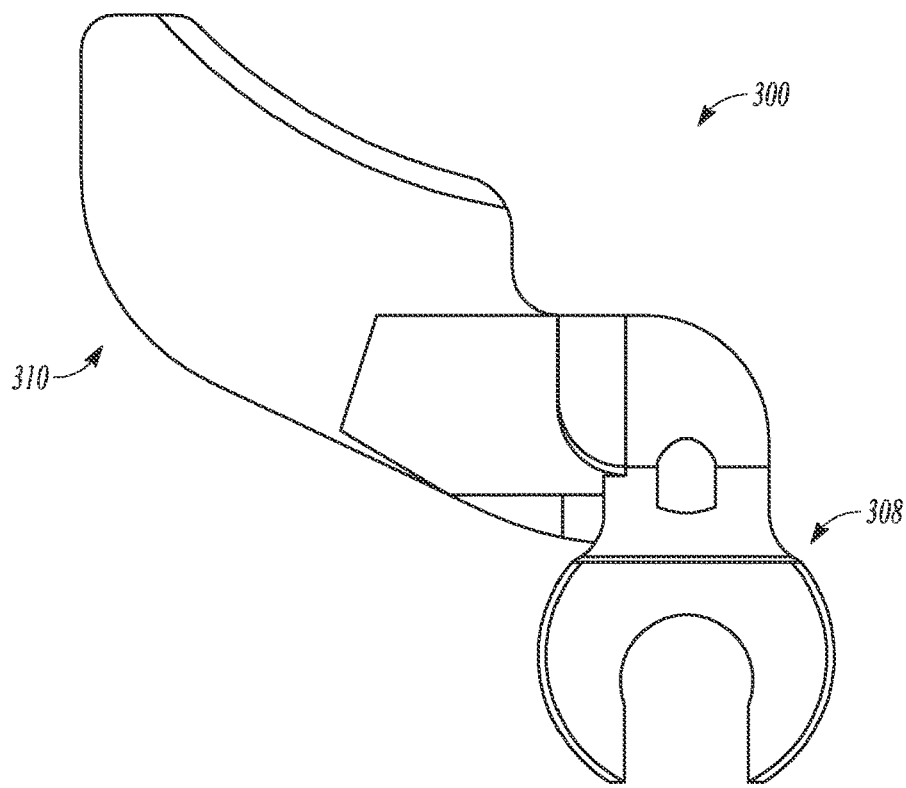
FIG. 7F is a plan view of a distal side of the cut guide of FIG. 7 according to example of the present application.

FIGS. 7 to 7F illustrate a cut guide 300 according to another example. The cut guide 300 can have of a similar construction to that of cut guide 200; however, certain aspects of the construction can differ. Like the cut guide 200, the cut guide 300 can include a mounting portion 308 and a cutting portion 310. The cutting portion 310 can include a capture 312 for the proximal cut and an aperture 320 as shown in FIG. 7A.

Cut guide 300 comprises a lateral cut guide. Thus, the cutting portion 310 can be offset from the mounting portion 308 in a lateral direction. In the examples of FIGS. 7 to 7F, the mounting portion 308 can be configured to couple with an alignment mechanism (not shown) similar to as illustrated and described previously. The cutting portion 310 can be connected to the mounting portion 308 (e.g., integral therewith so as to comprise a single component). As previously described, the cutting portion 310 defines the capture 312 (e.g., a slot) for the proximal cut.

The cutting portion 310 can also have the aperture 320 disposed adjacent a first end 314 of the capture 312. The aperture 320 can extend generally anterior-posterior while the capture 312 can extend both anterior-posterior and proximal-distal (e.g. the capture 312 can be defined to have a small degree of distal down angle from the anterior to posterior). As illustrated in FIG. 7A, the cutting portion 310 around the aperture 320 can form a counterbore 320A configured to receive a head of the stop component (e.g., stop component 118 of FIGS. 5 and 5A) therein. The counterbore 320A can be contacted by the head to aid in holding the cut guide 300 against the knee.

Figure 8:
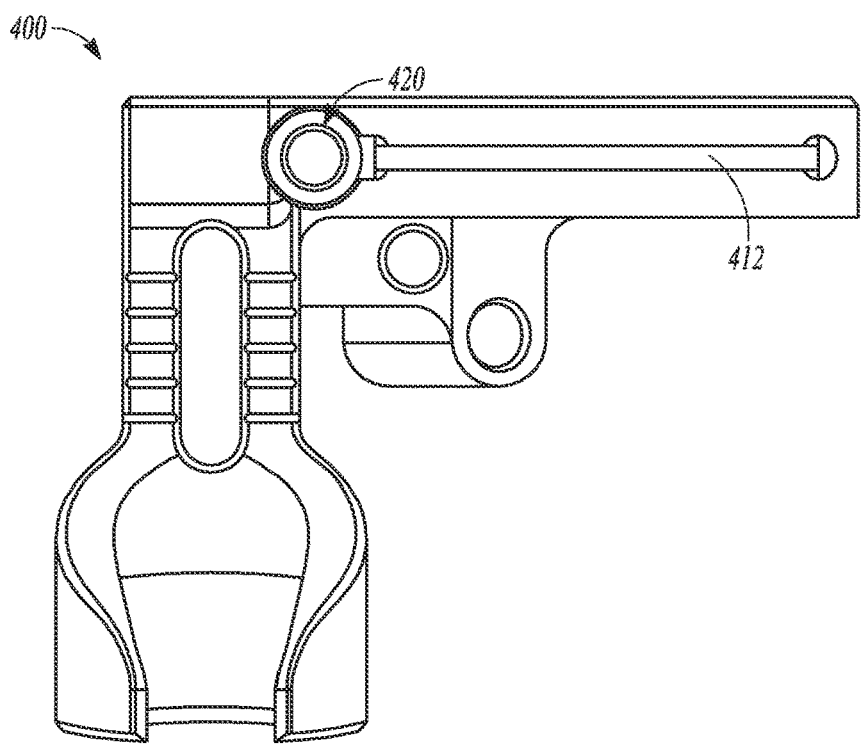
FIG. 8 is a plan view of an anterior side of a cut guide according to another example of the present application.

As shown in FIGS. 7 and 7A the aperture 320 can be spaced from the capture 312 (e.g., can have a part of the cutting portion 310 disposed between the aperture 320 and the capture 312). However, in other examples, the aperture 320 can be in communication with the capture 312. FIG. 8 illustrates such an arrangement with a cut guide 400 where the aperture 420 is in communication with the capture 412.

As discussed previously, the aperture 320, 420 is configured to receive the stop component, which can act to limit travel of the saw performing resection of the knee. Thus, sensitive areas such as the intercondylar eminence and/or the posterior cruciate ligament (PCL) can be spared contact with the saw during the proximal and/or sagittal resection allowing them to be better preserved.

Figure 9:
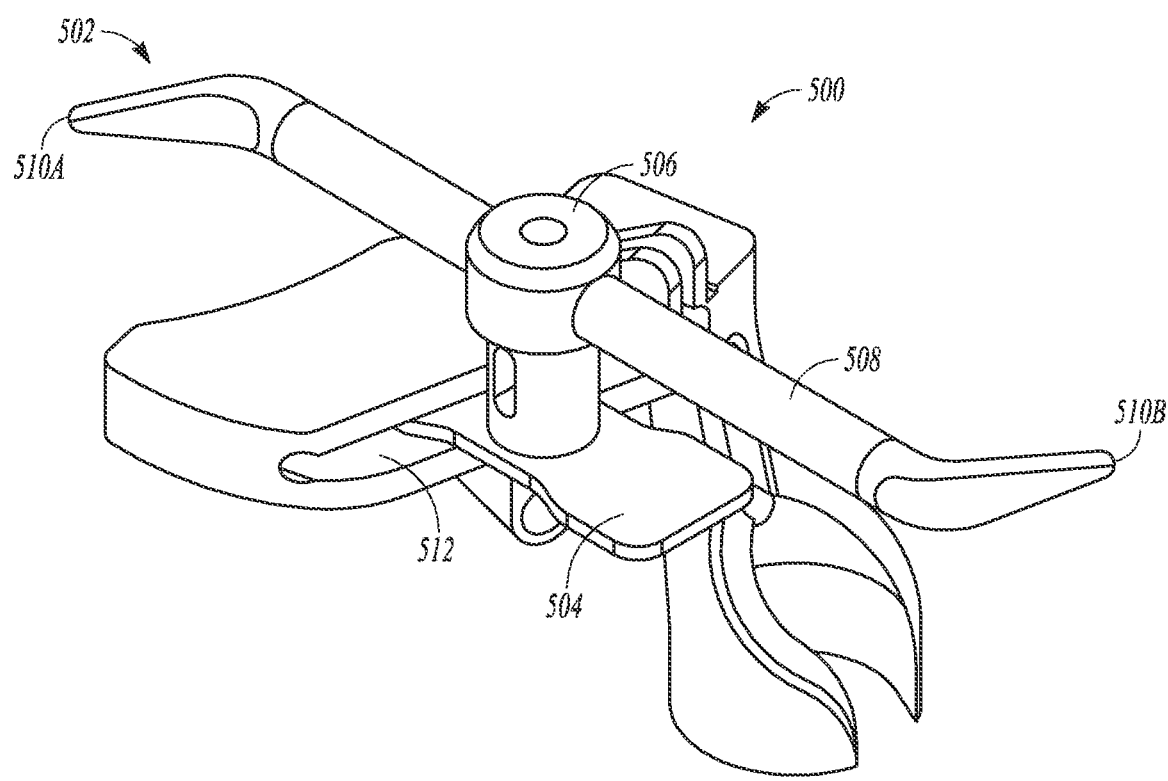
FIG. 9 is perspective view of a stylus mounted to cut guide according to an example of the present application.
Figure 9A:
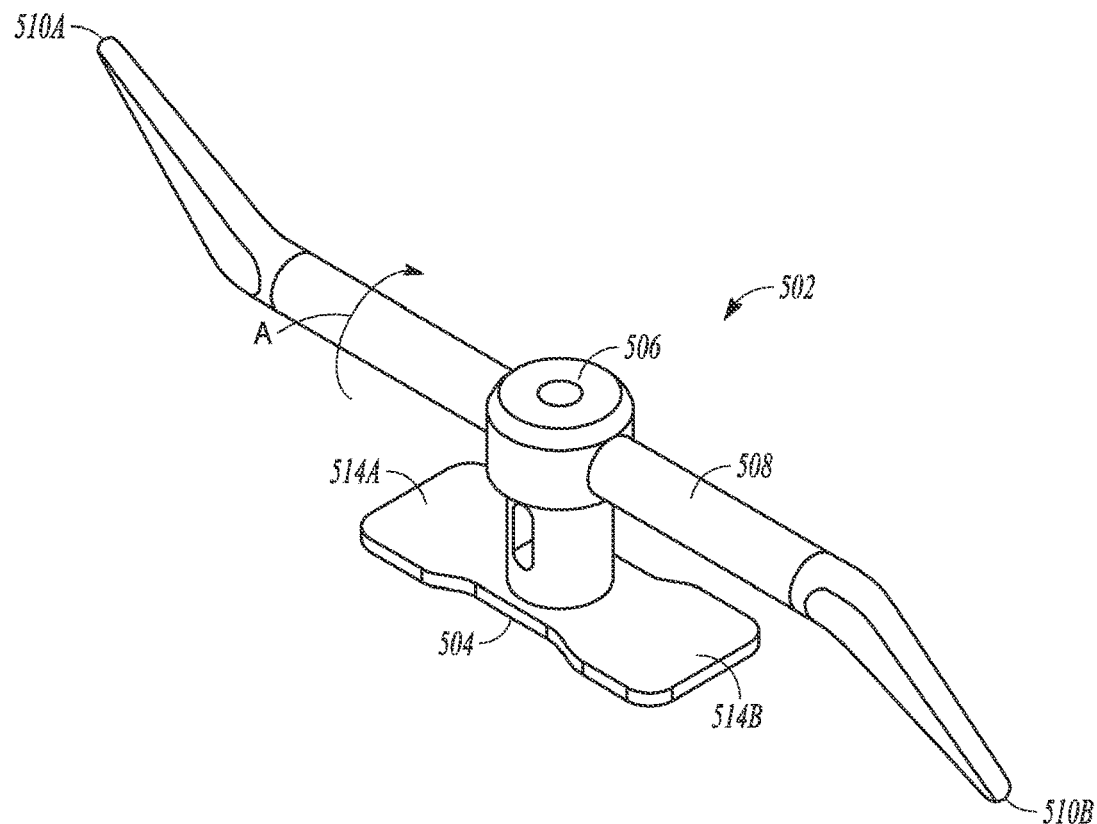
FIG. 9A is a perspective view of the stylus of FIG. 9 according to example of the present application.

FIGS. 9 and 9A illustrate a stylus assembly 502 that can be mounted to a cut guide 500 (FIG. 9). The cut guide 500 can include any of the cut guides previously described and other cut guides not explicitly shown or described. The stylus assembly 502 can include a base 504, a body 506, a boom 508, a first tip 510A, and a second tip 510B.

FIG. 9 illustrates that the stylus assembly 502 can be configured to be received in the proximal capture 512 of the cut guide 500. When received in the capture 512, the first tip 510A can be configured to reference the capture 512 a predetermined distance (e.g., 2 mm) from an anatomical landmark (e.g., a deepest defect on the tibial plateau) in a first position. Similarly, when received in the capture 512, the second tip 510B can be configured to reference the capture 512 a second predetermined distance (e.g., 4 mm) from the anatomical landmark in a second position.

More particularly, as shown in FIG. 9A, the base 504 can include substantially similar first and second portions 514A and 514B. Either portion can be insertable into the capture 512 (FIG. 9) allowing either the first tip 510A or the second tip 510B to extend over the tibia and act as the reference as described above. The body 506 connects to the base 504 and extends generally proximally therefrom and can be configured to receive the boom 508 therein. The boom 508 can be rotatable relative to the body 506 and the base 504 to adjust the position of the first tip 510A and the second tip 510B.

After mounting of the stylus assembly 502 to the cut guide 500, the boom 508 can be rotated from the position of FIG. 9A to the position of FIG. 9 (as indicated by arrow A) to reference the anatomical landmark using the first tip 510A.

The first tip 510A and the second tip 510B can be angled differently from one another relative to the boom 508 providing for different proximal termination locations. As described above, such termination locations can be configured to reference different predetermined distances (e.g., 2 mm and 4 mm) of the capture 512 from the anatomical landmark. In this manner the proximal-distal location of the cut guide 500 relative to the knee can determined.

To reference the anatomical landmark using the second tip 510B, the position of the stylus assembly 502 can be reversed such that the second portion 514B of the base 504 is received in the capture 512. According to other examples, the body 506 can be configured to be rotatable relative to the base 504 to position the second tip 510B to reference the anatomical landmark.

Figure 10:
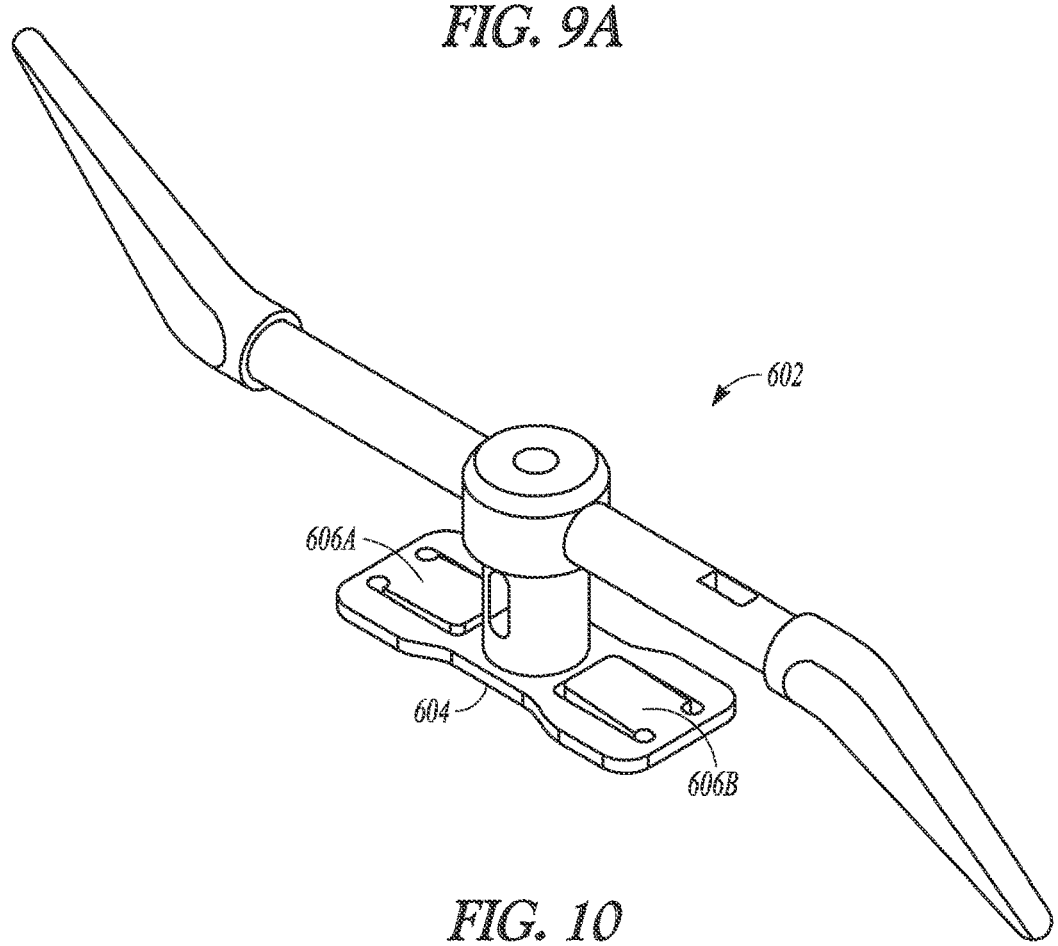
FIG. 10 is a perspective view of a stylus according to another example of the present application.

FIG. 10 illustrates a stylus assembly 602 according to another example. The stylus assembly 602 includes a base 604 with spring members 606A and 606B. The spring members 606A and 606B are adapted to contact the cut guide when the base 604 is inserted into the capture. The spring members 606A and/or 606B can aid the stylus assembly 602 in mounting to the cut guide.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The invention claimed is:

1. An apparatus for guiding a tibial bone cut during knee replacement surgery, the apparatus comprising:
a mounting portion configured to couple with an alignment mechanism; and
a cutting portion connected to the mounting portion and defining a first capture for a proximal cut, the cutting portion having a second capture for a sagittal cut;
wherein at least a portion of the second capture is defined by a plurality of projections extending proximally from a proximal surface of the cutting portion, wherein the plurality of projections taper toward the proximal surface from anterior to posterior.

2. The apparatus of claim 1, wherein the cutting portion is offset from the mounting portion in at least one of a medial or lateral direction and the first capture is configured to define a medial-lateral cut length such that the proximal cut is to a single compartment of a knee.

3. The apparatus of claim 1, wherein the cutting portion has an aperture disposed adjacent a first end of the first capture, and wherein the aperture is in communication with the second capture.

4. The apparatus of claim 3, wherein the first capture communicates with the aperture.

5. The apparatus of claim 3, wherein the aperture is disposed adjacent a first end of the second capture.

6. The apparatus of claim 1, wherein the mounting portion includes a slot configured to receive a fastener, the slot configured to allow for proximal-distal adjustment of the apparatus relative to a knee, the mounting portion having indicia disposed adjacent the slot for referencing movement of the apparatus relative to the fastener.

7. The apparatus of claim 1, further comprising a second mounting portion having a plurality of mounting holes therethrough, at least one of the plurality of mounting holes arranged substantially parallel with an aperture in the cutting portion and at least a second of the plurality of mounting holes arranged oblique to the aperture.

8. An apparatus for guiding a tibial bone cut during knee replacement surgery, the apparatus comprising:
a mounting portion configured to couple with an alignment mechanism; and
a cutting portion connected to the mounting portion and defining a first capture for a proximal cut, the cutting portion having a second capture for a sagittal cut;
wherein at least a portion of the second capture is defined by a plurality of projections extending proximally from a proximal surface of the cutting portion;
wherein the plurality of projections comprise a pair of medial-lateral spaced projections and the second capture comprises three captures comprising:
a laterally disposed capture defined by a first surface of a first of the pair of projections;
a medially disposed capture defined by a first surface of a second of the pair of projections, and
a middle capture defined by a second surface of the first of the pair of projections and defined by a second surface of the second of the pair of projections, wherein the cutting portion has an aperture disposed adjacent a first end of the first capture, and wherein the aperture is in communication with the second capture, and wherein the first capture communicates with the aperture.

9. The apparatus of claim 8, wherein the cutting portion is offset from the mounting portion in at least one of a medial or lateral direction and the first capture is configured to define a medial-lateral cut length such that the proximal cut is to a single compartment of a knee.

10. The apparatus of claim 8, wherein the aperture is disposed adjacent a first end of the second capture.

11. The apparatus of claim 8, wherein the aperture is configured to receive a fastener.

12. The apparatus of claim 8, further comprising a second mounting portion having a plurality of mounting holes therethrough, at least one of the plurality of mounting holes arranged substantially parallel with an aperture in the cutting portion and at least a second of the plurality of mounting holes arranged oblique to the aperture.

13. An apparatus for guiding a tibial bone cut during knee replacement surgery, the apparatus comprising:
a mounting portion configured to couple with an alignment mechanism; and
a cutting portion connected to the mounting portion and defining a first capture for a proximal cut, the cutting portion having a second capture for a sagittal cut:
wherein at least a portion of the second capture is defined by a plurality of projections extending proximally from a proximal surface of the cutting portion;
wherein the plurality of projections comprise a pair of medial-lateral spaced projections and the second capture comprises three captures comprising:
a laterally disposed capture defined by a first surface of a first of the pair of projections;
a medially disposed capture defined by a first surface of a second of the pair of projections, and
a middle capture defined by a second surface of the first of the pair of projections and defined by a second surface of the second of the pair of projections, wherein the three captures are spaced substantially 3 mm apart from one another in a medial-lateral direction.

* * * * *

UNITED STATES PATENT AND TRADEMARK OFFICE
CERTIFICATE OF CORRECTION

PATENT NO. : 12,290,272 B2  
APPLICATION NO. : 17/853492  
DATED : May 6, 2025  
INVENTOR(S) : Jones et al.

Page 1 of 1

It is certified that error appears in the above-identified patent and that said Letters Patent is hereby corrected as shown below:

In the Claims

In Column 14, Line 44, in Claim 13, delete "cut:" and insert --cut;-- therefor

Signed and Sealed this
First Day of July, 2025

Coke Morgan Stewart
*Acting Director of the United States Patent and Trademark Office*